United States Patent [19]
Ruano et al.

[11] Patent Number: 5,972,614
[45] Date of Patent: Oct. 26, 1999

[54] GENOME ANTHOLOGIES FOR HARVESTING GENE VARIANTS

[75] Inventors: Gualberto Ruano, New Haven; Kevin L. Bentley, Madison; Frank H. Ruddle, New Haven, all of Conn.

[73] Assignee: Genaissance Pharmaceuticals, New Haven, Conn.

[21] Appl. No.: 08/987,966

[22] Filed: Dec. 10, 1997

Related U.S. Application Data

[63] Continuation-in-part of application No. 08/761,704, Dec. 6, 1996, Pat. No. 5,866,404
[60] Provisional application No. 60/032,645, Dec. 10, 1996, and provisional application No. 60/008,250, Dec. 6, 1995.

[51] Int. Cl.$^6$ .............................. C12Q 1/68; C12N 1/19; C12N 5/10; C12N 15/10
[52] U.S. Cl. ...................... 435/6; 435/254.11; 435/254.2; 435/255.1; 435/320.1; 435/440
[58] Field of Search ...................... 435/6, 320.1, 172.1, 435/172.3, 254.11, 254.2, 255.1, 440

[56] References Cited

FOREIGN PATENT DOCUMENTS

WO 98/01573   1/1998   WIPO .

OTHER PUBLICATIONS

Degryse et al. In Vivo Cloning by Homologous Recombination in Yeast Using a Two–Plasmid–Based System. *Yeast.* 11: 629–640, 1995.
Burke et al. Cloning of Large Segments of Exogenous DNA into Yeast by Means of Artificial Chromosome Vectors. *Science.* 236: 806–812, May 1987.
Bradshaw et al., (1993) 1$^{st}$ European Science Foundation Conference on Developmental Biology, Karause Ittengen, Switzerland Jun. 14–17.
Bradshaw et al., (1995) *Acids Res.* 23:4850–4856.
Bradshaw et al., (1996) *Proc. Natl. Acad. Sci. USA* 93:2426–2430.
Burgers and Percival, (1987) *Analyt. Biochem.,* 163:391–397.
Campbell et al., (1991) *Proc. Natl. Acad. Sci. USA* 88:5744–5748.
Campbell et al., (1995) *Nucl. Acids Res.* 23:3691–3695.
Erickson and Johnston (1993) *Genetics* 134:151–157.
Frengen et al., (1997) *Genetic Analysts: Biomolecular Engineering* 14:55–59.
Ketner et al. (1994) *Proc. Natl. Acad. Sci. USA* 91:6186–6190.
Kogoma, (1997) *Microbiol. Mol. Biol. Reviews* 61:212–238.
Kouprina et al., (1994) *Genomics* 21:7–17.
Larionov et al., (1994) *Nucl. Acids. Res.* 22:4154–4162.
Larionov et al., (1966a) *Proc. Natl. Acad. Sci. USA* 93:491–496.
Larionov et al., (1996b) *Proc. Natl. Acad. Sci. USA* 93:13925–13930.
Larionov et al., (1997) *Proc. Natl. Acad. Sci. USA* 94:7384–7387.
McGonigal et al., (1995) *Gene* 155:267–271.
Miller et al., (1993) *Genes & Dev.* 7:933–947.
Orr–Weaver, et al., (1983a) *Proc. Natl. Acad. Sci., USA* 78:6354–6358.
Orr–Weaver, et al., (1933b) *Meth. Enzymol.* 101:228–245.
Pavan et al., (1990) *Proc. Natl. Acad. Sci. USA* 87:1300–1304.
Sikorski and Hieter (1989) *Genetics* 122:19–27.
Simpson and Huxley (1996) *Nucl. Acids. Res.* 24:4693–4699.
Spencer et al., (1993) *Methods: A Companion to Methods in Enzymology* 5:161–175.
van Dijk et al., (1997) *Cancer Res* 57:3478–3485.

*Primary Examiner*—Nancy Degen
*Attorney, Agent, or Firm*—Morgan & Finnegan, L.L.P.; Eugene Moroz; Dorothy R. Auth

[57] ABSTRACT

The present invention relates to the development of collections of a single gene locus from a collection of individuals or organisms, called genome anthologies. The invention describes several novel methods for producing collections of a gene or gene families from multiple individuals or organisms. One method is targeted in vivo cloning. Another method is locus specific primer extension and exonuclease degradation method.

4 Claims, 19 Drawing Sheets

Denature Genomic DNA
Primer annealing to site flanking locus
Extension by thermostable DNA polymerase Exonuclease VII digestion
Clone into anthologies

GENOME ANTHOLOGIES FOR HARVESTING GENE VARIANTS

This is a regular application of co-pending provisional applications Ser. No. 60/032,645 filed Dec. 10, 1996 and Ser. No. 60/008,250 filed Dec. 6, 1995 which is a CIP of U.S. Ser. No. 08/761,704 filed Dec. 6, 1996, now U.S. Pat. No. 5,886,404.

FIELD OF THE INVENTION

The present invention relates to the field of genomics and the development of genome anthologies. The present invention also relates to the use of such genome anthologies to screen patients for sensitivity to specific drugs. The present invention also relates to the isolation of naturally occurring gene targets for pharmaceutical development. The present invention also relates to the correlation of genotype to phenotype in specific individual genomes.

BACKGROUND OF THE INVENTION

Analysis of genetic population structure of any organism at the molecular level, requires a thorough understanding of the nature and distribution of DNA sequences among its component individuals and populations. Techniques used in such studies have included allele frequency data (Bowcock, 1987), restriction fragment length polymorphisms (Botstein et al., 1980) and by discovering association among loci for mapping both simple (Collins, 1995) and complex diseases (Lander et al 1989). Similarly, a wealth of data have emerged from studies on the maintenance and evolution of DNA sequences in specific areas of the Drosophila genome such as Adh (Krietman 1983), Xdh (Riley et al., 1989) and amylase (Aquadro et al., 1991). Clearly, a detailed analysis of genomic regions and the genealogy of these genomes across populations, species and genera, using a variety of highly innovative techniques toward the construction of high density haplotypes, and sequence analysis of specific regions would yield information not only on the genome diversity among populations, their aggregates and species but also reveal the significance of diversity at the phenotypic level.

The study of haplotype (haploid genotype) diversity has been recognized as an important tool for studying evolutionary lineages among populations (Templeton et al 1987)) as well as establishing associations and linkage or gametic disequilibria among loci. Since 1989, several methodologies for haplotyping individual genetic markers at specified loci have been investigated using strictly molecular means. The concept of linkage disequilibrium, defined as non-random associations of alleles among loci, plays an important role in mapping genes that are valuable in population, anthropological and medical research. In addition, polymorphic short tandem repeat markers (STR) have been employed to obtain informative haplotypes for linkage analysis (Weber & May, 1989; Dubovsky et al., 1995). However, the use of such haplotype systems is compromised by frequent instances of ambiguous linkage phase in a population sample. Although genotyping of pedigrees often allows determination of linkage phase for many populations of medical and anthropological interest, material on informative families is often unavailable or inadequate. Furthermore, robust statistical methods to estimate haplotype frequencies (Excoffier & Satkin, 1995) often mis-identify rare haplotypes and occasionally generate spurious haplotypes (Tishkoff et al., 1996b). Hence, new and accurate molecular methods for generation of haplotypes are urgently needed.

Methods to isolate genes and specific loci can be grouped into the following two broad categories: construction of genomic DNA libraries and the polymerase chain reaction (PCR). First, production and maintenance of genomic libraries is not only labor intensive, but also requires at least three fold over-sampling to meet the odds of recovering the specific locus. Occasional under-representation of specific regions due to variations in the method of construction of libraries, cloning vectors and stochiasticity associated with biological systems, further increases the uncertainty of recovering a well-defined region of interest. Thus, library construction and screening to study molecular genetic diversity of a large number of individuals across several populations and species will become a formidable task.

Alternatively, while PCR methods offer rapid and efficient analysis of specific loci, there is a limitation on the size of the sampled region. Current methods can accommodate up to 35 kb using cloned DNA as template (Barnes, 1994), but only 25 kb from complex genomic DNA (Cheng et al., 1994). Additionally, optimizations of conditions for long range PCR of genomic DNA, coupled with the introduction of sequence errors during amplification, pose serious problems in the comparative analysis of DNA sequence variation of a specific region among individuals and populations. Directly cloning the desired region from native genomic DNA would provide an effective alternative to library construction and PCR.

One object of the present invention relates to methods for generating collections of a single genetic locus from various sources.

Another object of the present invention relates to genome anthologies, that is, collections of a specific locus, including, for example, a gene or group of genes from multiple sources.

Another object of the present invention relates to the generation of genome anthologies from all members of a gene family from one source or from multiple sources.

Yet another object of the present invention relates to the use of such genome anthologies in a method for identifying specific haplotyping targets.

A further object of the present invention relates to novel methods for haplotyping individual genetic markers at specified loci.

Yet another object of the present invention relates to harvesting human DNA variants to generate targets for drug discovery.

A further object of the present invention relates to the use of haplotyping to screen individuals for sensitivities to specific drugs or treatment regimes.

Another object of the invention is the development of molecular haplotyping kits for a several loci distributed throughout the human genome.

Another object of this invention is to collect multiple variants of a single complete gene from different members of a population, in a manner that not only is efficient, but results in a permanent, replicatable, expressible, fully manipulatable, individually identifiable collection of hemizygous entities.

Another object of this invention is to use genetic variation 1) to enhance the efficacy of therapeutics by customizing such genetic variation for specific population groups, 2) to reduce the costs of developing new drugs, and 3) to increase the chances that a new drug will be successful in clinical trials and, therefore, gain FDA approval.

SUMMARY OF THE INVENTION

The present invention relates to collections of a single genetic locus or loci comprising a gene family isolated from various sources, and methods of generating such genomic collections. These collections, known as genome anthologies, are useful in identifying haplotypes, identifying drug targets and determining sensitivities to reagents based upon genetic determinants and/or genetic variability.

One method for generating genome anthologies employs targeted in vivo cloning ("TIVC"), providing simultaneous genome targeting and locus isolation. This method allows generation of specific haplotyping targets from any number of individuals in a population. In this embodiment, up to 300 kb of DNA can be cloned, permitting ready analysis of linkage disequilibrium as a function of distance, by sampling markers across large hemizygous regions and for recovering entire genes, including regulatory regions many kilobases away from the coding region.

Yet another embodiment of the present invention is to harvest all members of a gene family by means of TIVC. This is accomplished by employing, specific "signature," or conserved sequences, common to all gene family members to retrieve all members of the gene family regardless of their chromosomal location.

Yet another method for generating genome anthologies may be employed. Long range PCR can be used to accommodate as much of a locus as possible. In particular, this method is useful in cases where a very specific DNA region is targeted. This method comprises (i) polymerase chain reaction from a plurality of DNA templates; (ii) cloning of the PCR products into a vector; and (iii) analysis of the variants in isolation for genotyping, expression and sequence variation. Genome anthologies may also be generated by employing a method which combines long range primer extension and exonuclease treatment in the targeting step.

DETAILED DESCRIPTION OF THE INVENTION

Figure 1:
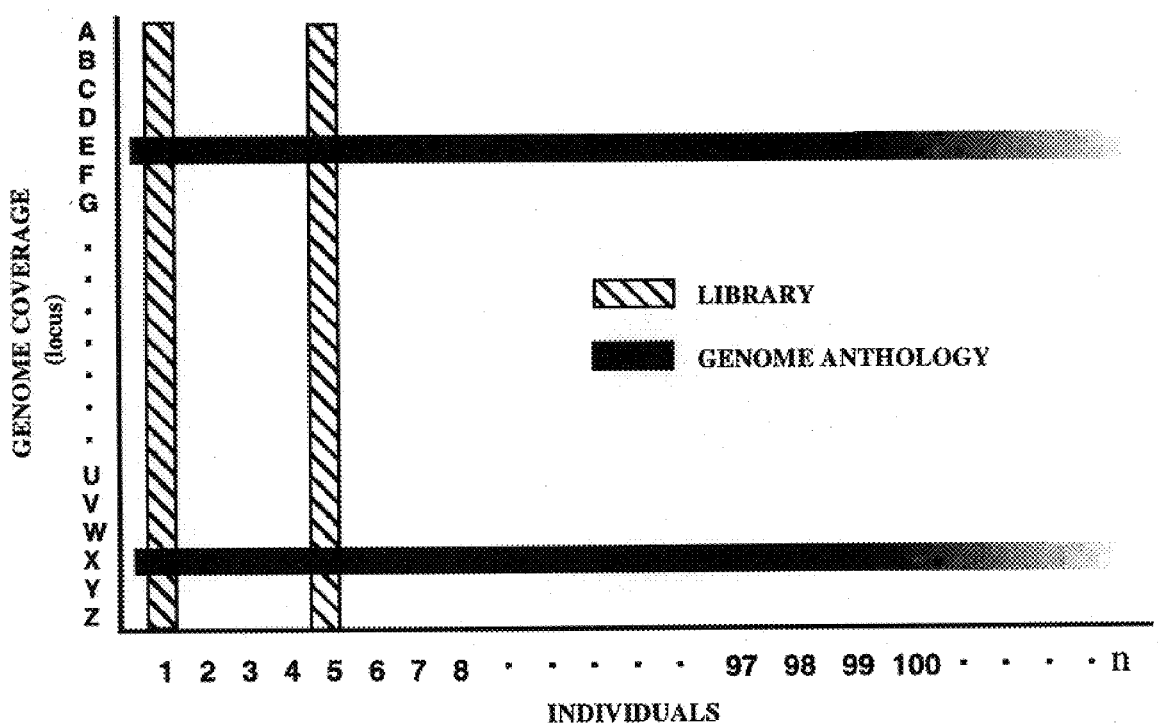
FIG. 1. Comparison of a genomic library with a genome anthology. Genomic libraries are collections of all genetic loci present in the genome of an individual.

The present invention relates to genomic collections of a single locus, called genome anthologies and to new methods for generating such genomic collections. The present invention provides methods for isolating templates from DNA samples of individuals. These collections of a single locus provide a new resource of information, useful in diagnosing an individual's condition or disease state. The present invention also relates to a new method for molecular haplotyping. Further the genome anthologies, when contained in expression cell lines, allow correlation between a haplotype and an alteration in the gene's expression levels, or structural changes in the gene product that result in altered function.

One use of a genome anthology is to determine the exact composition and frequency of haplotypes of a given gene in a population. For example, targeted in vivo cloning ("TIVC") is used to recover the gene for the Endothelin A receptor (ENDRA) from a statistical cross-section of the North American population. Each member of the ENDRA genome anthology is determined. The resulting data is valuable for studies on population diversity, anthropological lineage, the significance of diversity and lineage at the phenotypic level, and for establishing control haplotypes and frequencies of "normal" populations for comparison with disease states.

Another use of a genome anthology is in establishing associations between candidate genes and disease states. A genome anthology prepared for a disease candidate gene X, in either an extended family or a population collected for the presence of the disease, can be analyzed to determine the frequency of association of the disease with a specific haplotype of gene X, and in the case of multifactorial disease, the contribution of gene X to the disease.

Another use of genome anthologies is to make risk assessments for disease in populations. Comparisons can be made among anthologies generated from normal and disease population or families to determine the frequency with which the disease haplotype occurs in each population.

Another use of a genome anthology is to determine the specific contributions of haplotypes to disease etiology. The haplotypes of a gene, whose association with a disease has been established, will consist of variation residing in coding or regulatory regions of the gene. Variation in these regions may be critical to the structure and regulation of the gene product and contribute to the aberrant phenotype. Such causal or contributory relationships can be established by 1) analyzing the genome anthology for variation that could potentially affect phenotype, and 2) by developing and expressing the genome anthology in a model system of the disease.

Another use of a genome anthology is to diagnose disease in an affected individual. By recovering disease genes from a patient by TIVC, the patient's haplotypes can be determined and compared to a database of haplotype information prepared from pre-established genome anthologies created for the disease genes.

Another use of a genome anthology is to generate targets for developing therapeutics. Genome anthology targets can be used to prioritize lead compounds or to find lead compounds that have the most pervasive activity in all targets of relevance for a given disease. For example, the constituents of a genome anthology created for the ENDRA gene could be expressed in a mammalian cell line to develop a simple screening assay for drug compounds that bind to the receptor and elicit a specific response. The variation that occurs among the different members of the ENDRA genome anthology may affect the binding affinity of the compound, and/or affect the cellular response to the signal triggered by binding. Correlations can then be made between a specific haplotype for ENDRA and the structure activity relationship (SAR) of a compound or group of compounds.

Another use of a genome anthology is to determine patient sensitivities to specific drugs or treatment regimes. Genetic variability is a determinant of patient response to therapy in terms of both efficacy and side effects. The genome anthology can be used in this manner for both new and existing drugs. For example, by using genome anthologies to correlate a specific haplotype with a disease, and by using the genome anthology as targets for drug screening and development, it is possible to create a prognostic test for customizing therapy based on the patient's genotype. Alternatively, during clinical trials for a drug, a genome anthology can be created for the target gene from all members of the trial group and used to make correlations between genetic variation and treatment response. This information can then be used to determine the proper therapeutic regime for a patient with a given genetic makeup.

"Primers," as the term is used herein, refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, i.e. in the presence of nucleotides and an inducing agent such as DNA polymerase and at a suitable temperature and pH. The primers are preferably single stranded for maximum efficiency in amplification, but may alternatively be double stranded. If double stranded, the primer is first treated to separate its strands before being used to prepare amplification products. Preferably, the primers are oligodeoxyribonucleotides at their 3' end. Primers can be entirely composed of DNA nucleotides or may contain PNAs or other nucleotide analogs at their 5' end. The primers must be sufficiently long to prime the synthesis of extension products in the presence of the inducing agent. The exact lengths of the primers will depend on many factors, including temperature, source of primer and use of the method. For diagnostic methods, the primers typically contain at least 10 or more nucleotides. It is also possible to use a primer which has been isolated from a biological source. One such example may be a restriction endonuclease digest of a large nucleic acid molecule.

"Genome anthologies" as the term is used herein, means a collection of hemizygous samples, from a single locus or members of a gene family, from multiple individuals of a defined population (FIG. 1). Genome anthologies are collections of defined loci from multiple individuals of a population selected by a common criterion. The term "locus" as it is used herein refers to any specific region of DNA, a gene, a group of genes or any group of nucleotides defining a DNA region of interest.

Haplotype systems involve multiple markers sufficiently closely linked that their inheritance is correlated and the effects of random genetic drift on them are not independent. Haplotypes may include, but are not limited to RFLPs (restriction length polymorphisms), microsatellites, short tandem 2–5 bp repeats, (Weber & May, 1989), bi-allelic markers, single base polymorphisms and insertion/deletions.

The genome anthologies of the present invention can be generated by the method comprising the steps of: obtaining a plurality of DNA samples; targeting a locus suspected of being in the DNA samples; and isolating the locus which is targeted. The DNA samples may be obtained by pooling DNA samples. Such a pooling step may combine two or more DNA samples from different sources. The sources may, for example, be different in that they are derived from different organs of a single individual, different individuals, different ethnic or nationality groups, different sexes, different populations or different organisms. Generally, any sources of DNA may be pooled for the creation of a genome anthology. "Pooling" comprises the combining of or mixing of the samples.

The targeting step of the instant invention may be carried out by one of several technologies. Many such targeting technologies are sequence determined. For example, long range primer extension may be used. This technique requires knowledge of the sequence flanking the targeted region. Alternatively nuclease digestion may be used to specifically cleave a genomic sequence at points flanking the target region. Other alternatives for the targeting step use other features of the genomic DNA, including but not limited to topology, protein-binding sites and membrane attachment sites. These features may be used to identify and target the sequence to be collected in the genome anthology.

Additionally, targeting may require allele specificity. One method of generating allele specificity uses an allele specific oligonucleotide in combination with a primer extension reaction and exonuclease degradation to generate hemizygous DNA targets.

Further, targeting of the locus may be accomplished by functional means. A locus that conveys a selective advantage when transformed into a deficient cell for that locus will be propagated advantageously. This locus from transfected variants can also become an anthology.

Generation of genome anthologies by TIVC requires specific targeting of the desired locus and high frequencies of recombination, particularly when pooled DNAs from a number of individual genomes are used. Co-transformation protocols to obtain high levels of recombination can be optimized in varius ways.

One method of enhancing the recombination frequency is to supplement the DNA with proteins involved in the recombination event. One such protocol uses Rad51, the yeast homolog of bacterial RecA (Shinohara et al. 1993; Kogoma, 1997). During the homologous recombination process, Rad51 catalyzes homologous pairing and strand exchange between single-stranded DNA and double-stranded DNA. pClasper targeting vectors may be constructed such that the cut ends of the recombinogenic arms are rendered single-stranded for a portion of their length by exonuclease digestion. Prior to co-transformation of yeast, the pClasper with single-stranded recombinogenic ends is mixed with the Rad51 protein. Rad51 protein binds to the single-stranded portions of the recombinogenic arms and upon co-transformation of yeast, facilitates recombination with the target DNA sequence.

Another example method for increasing the recombination frequency pre-targets the desired locus and unravels and stabilizes that area of DNA to promote access by pClasper. Jankowsky et al. (1997) have shown that the binding of short PNAs or oligonucleotides to regions flanking the hammerhead catalytic sequence in RNA molecules enhances the activity of ribozymes. Presumably, binding of the PNA or oligomer alters higher order structures in the RNA that hinder the alignment and annealing of the ribozyme to the substrate. In a similar fashion for TIVC, short oligonucleotides or PNAs (9–12 mers) are synthesized complementary to sequences of the target locus that flank the recombinogenic sites. The annealed oligonucleotides or PNAs can exert a localized effect to constrain the genomic DNA in a more open, untangled manner. Such a configuration can make the recombinogenic sites more accessible for pClasper.

Yet another method involves modifications to the autonomous replication sequences (ARS) in pClasper. Human genomic DNA has ARS-like sequences that may be capable of providing the same function in yeast (Stinchcomb et al., 1980). Deleting this sequence from the vector may improve recombination frequencies by reducing the background caused by recircularization and replication of the vector in the absence of recombination. Genomic DNA targets that contain an ARS-like sequence can provide complementation for the deleted ARS sequence in pClasper. By targeted mutagenesis, a version of pClasper has been produced with a non-functional ARS sequence to take advantage of this possibility. In addition, by optimizing the co-transformation procedures as described previously (Example 1), a very low background has been achieved.

The isolation step of the present method may be accomplished by several steps known in the art, including but not limited to, standard cloning and amplification techniques. For example, amplification techniques include PCR (Mullis U.S. Pat. Nos. 4,683,202 and 4,683,795) LCR (EP Pat. No. 320,308), SDA (U.S. Pat. No. 5,455,166), and NASBA (U.S. Pat. Nos. 5,130,238; 5,480,784; U.S. Pat. No. 5,399,491). Cloning, as employed in the isolation step of the present invention, is described in detail in Sambrook et al. (1989).

Optionally, these isolated collections of a specific locus may be separated and individual variants may be analyzed.

Figure 2:
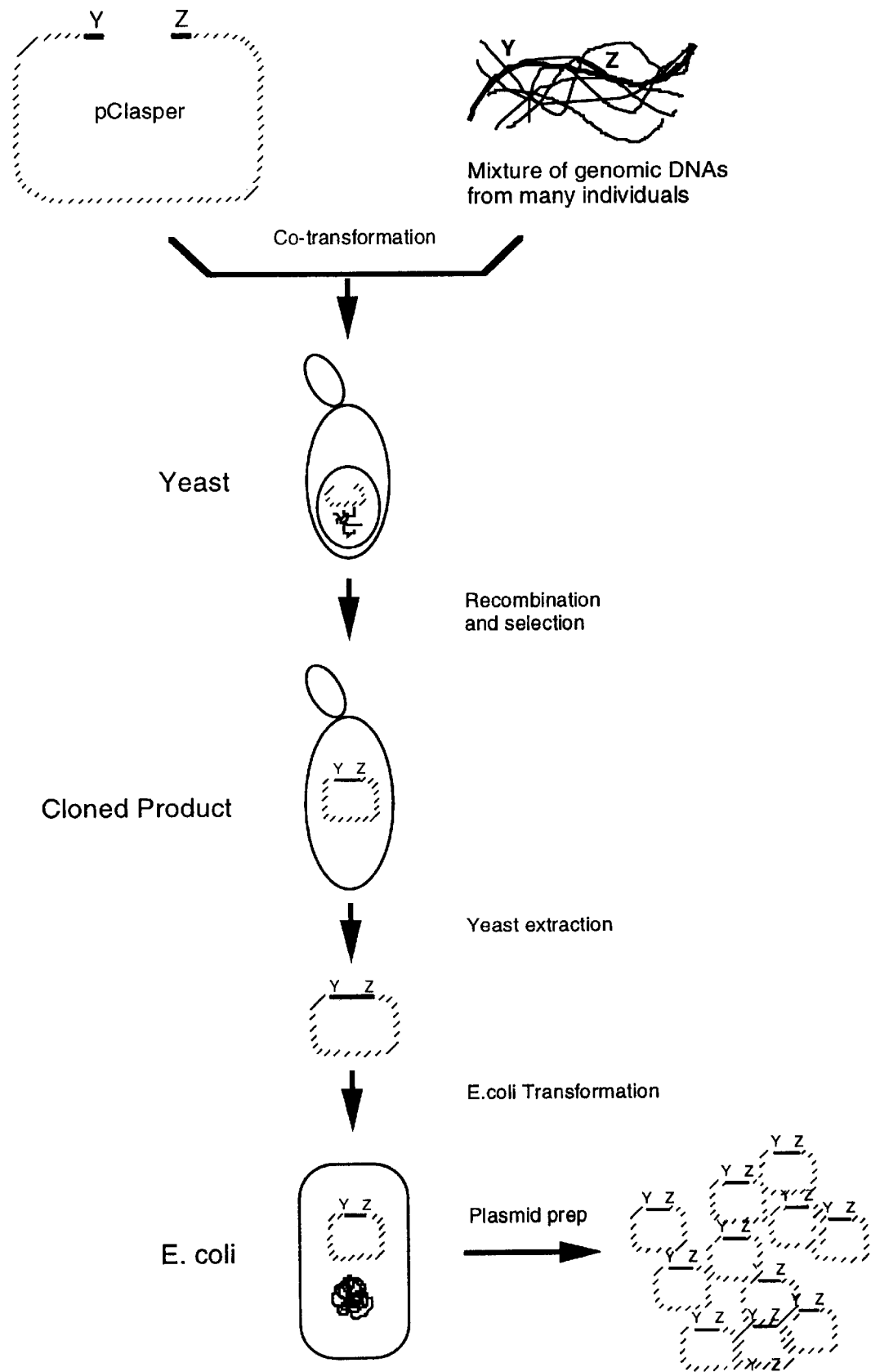
FIG. 2. Creation of a genome anthology by TIVC. An in vivo cloning vector, pClasper, equipped with sequences that target locations Y and Z in genomic DNA, is constructed and mixed with DNA pooled from individuals of a defined population. The mixture of genomic DNA and vector is used to co-transform yeast. By homologous recombination, the target DNA defined by sites Y and Z is rescued in the vector as hemizygous clones that can be shuttled to bacteria for amplification.

A particularly preferred embodiment combines the targeting and isolating steps of the method. In this embodiment of the present invention, a method for generating genome anthologies comprises targeted in vivo cloning in yeast using a yeast bacteria shuttle vector (FIG. 2). Up to 300 kb of DNA can be cloned by the targeted in vivo cloning method of the present invention, permitting ready analysis of linkage disequilibrium as a function of distance, by sampling markers across large hemizygous regions. Genome anthologies produced by the TIVC method are cloned hemizygous genomic DNA samples. The cloning aspect of the present invention facilitates the preservation of genome anthologies as permanent collections, as well as, the production of significant quantities of DNA from each sample. The yeast bacteria shuttle vector has recombinogenic ends homologous to specific regions in uncloned genomic DNA that flank the segment to be haplotyped and/or targeted. Yeast cells are co-transformed with the linearized vector and uncloned genomic DNA from one or more individual samples to be haplotyped. Preferably, pools of DNA from several individuals are used as the target template. By homologous recombination in yeast, the target region is rescued in the yeast bacteria shuttle vector as hemizygous clones that can be shuttled to bacteria for amplification. Significant quantities of hemizygous DNA from both haplotypes of each individual are thus made available for genotyping of all polymorphisms present in the haplotype.

One yeast bacterial shuttle vector used in TIVC comprises a yeast replication origin, a yeast selection marker gene, a bacteria replication origin, a bacteria selection marker gene and at least one unique cloning site. The yeast replication origin is used for replication and propagation in yeast. Examples of such elements are any of the known yeast autonomous replicating sequences (ARS) or centromeres (CEN). The yeast selection marker gene may be selected from a known gene capable of being selected for: such genes include but are not limited to genes encoding auxotrophic markers, such as LEU2, HIS3, TRP1, URA3, ADE2 and LYS2. Alternatively, genes encoding a protein conferring drug resistance on a host cell can be used as a yeast selection marker. Such genes include, but are not limited to CAN1 and CYH2. The bacterial replication origin is preferably selected from those replication origins used for stable bacterial replication of large DNA inserts, including the F factor and the P1 replicon. Other bacterial replicons may be used for smaller DNA inserts. Any of the many known bacterial selection marker genes may be used; examples of bacterial selection marker genes include genes conferring bacterial resistance to antibiotics, such as kanamycin, ampicillin, tetracycline, Zeocin, neomycin and hygromycin and chloramphenicol. Other antibiotic resistance genes are encompassed herein and are known to those skilled in the art.

One such yeast bacteria shuttle vector useful in the TIVC embodiment of the present invention comprises combinations of several vector features: 1) site-specific targeting, 2) yeast to bacterial (and bacteria to yeast) shuttle capability, 3) interchangeable recombinogenic ends, 4) large insert capacity, and 5) near universal compatibility with large insert cloning systems in bacteria and yeast. One such vector is known as pCLASPER, which was first described by Ruddle (Bradshaw et al, 1995). The present invention may use a yeast bacteria shuttle vector, such as pCLASPER to shuttle uncloned genomic DNA into bacteria for further analysis, such as haplotyping.

Transformed yeast DNA integrates into the yeast genome almost exclusively by homologous recombination. Free ends of DNA are highly recombinogenic, and recombination frequencies increase by several orders of magnitude when double-stranded breaks are made within homologous sequences carried on a plasmid (Orr-Weaver et al., 1981; 1983). When plasmids are linearized with a partial loss of homologous sequence information, the sequence gap is repaired by recombination with chromosomal sequences. In cases where plasmids contain more than one possible recombination site, gap-repair can be site-directed by linearizing the plasmid within a specific sequence. Selectable markers located on the plasmid permit high-frequency rescue of the gap-repaired plasmid. When a target gene in genomic DNA and the TIVC vector equipped with target recognition sequences are used to co-transform yeast, recombination preferentially takes place between the target and vector.

As part of a general experimental scheme (FIG. 2), the general procedures of Bradshaw et al. (1995) from recombinogenic end cloning to transfer of circularized recombinants into E. coli are followed. Standard PCR and molecular cloning techniques are used for preparing recombinogenic ends in pCLASPER. The pCLASPER construct is linearized at a unique site between the end sequences and used to co-transform yeast with the target DNA.

The TIVC method for creating genome anthologies relies on the high frequency of homologous recombination of yeast, for which an extensive body of knowledge exists. While the frequency of homologous recombination is much lower in mammalian systems, there is a great deal of ongoing research to determine the factors that control this activity. Methods to enhance and control the event frequency in mammalian cells is becoming available. current knowledge based on research of recombination stem cells (Mansour et al, 1988), and the development of mammalian artificial chromosomes (Huxley, 1997; Rosenfield, 1997; Harrington et al., 1997), makes it possible to create genome anthologies directly in human cells, thus eliminating the steps of isolating the human genomic DNA, mixing with a pClasper rescue vector, and co-transforming yeast. The method for TIVC in human cells (or with small modifications, any mammalian cells), would include a pClasper-like vector capable of stable, selectable, and autonomous replication in mammalian cells. The vector would include 1) human centromeric and telomeric sequences, 2) a selectable marker gene such as the neomycin resistance gene, and 3) recombinogenic ends for the target gene. Replication can be satisfied by sequences present in the genomic DNA to be rescued (i.e. ARS-like sequences). Optional capability of replication and selection in a bacterial host may be employed, primarily for ease in rescue and manipulation of the recombinant. Alternatively, it may be possible to modify vector types to be used for expression of genes in mammalian cells.

To perform TIVC in human cells, lymphocytes collected from a blood sample can be transformed with the human pClasper and recombination can take place between the human pClasper and the lymphocyte chromosomal DNA at the target site. The lymphocytes containing the recombinants are selected in tissue culture medium supplemented with neomycin.

In another embodiment of the present invention, a method for generating genome anthologies comprises a long-range primer extension step and an exonuclease degradation of single stranded DNA step, in multiply heterozygous genomic DNA. The primer extension step of the method may be primed with oligonucleotides. The oligonucleotide serves as an extension primer for DNA synthesis by a thermostable DNA polymerase starting from a polymorphic locus and extending to other polymorphic loci downstream or upstream. The resulting double stranded product is protected from exonuclease hydrolysis.

Figure 3:
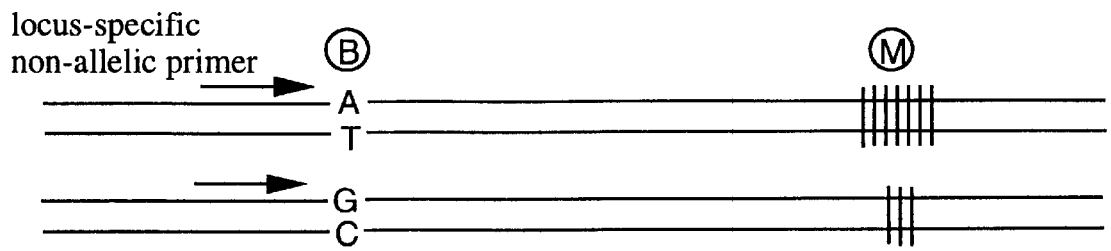
FIG. 3. Molecular haplotyping using a primer extension and exonuclease degradation method. This method generates selected loci from whole genome samples by selective protection from exonuclease degradation of the desired locus. Allele-specific strand extension using a thermostable DNA polymerase generates a double-stranded allele specific product that is not degraded in the presence of exonuclease that digests the remaining unprotected single-stranded genomic DNA. All polymorphic sites within the region extended from the allele-specific primer are also protected.
Figure 3:
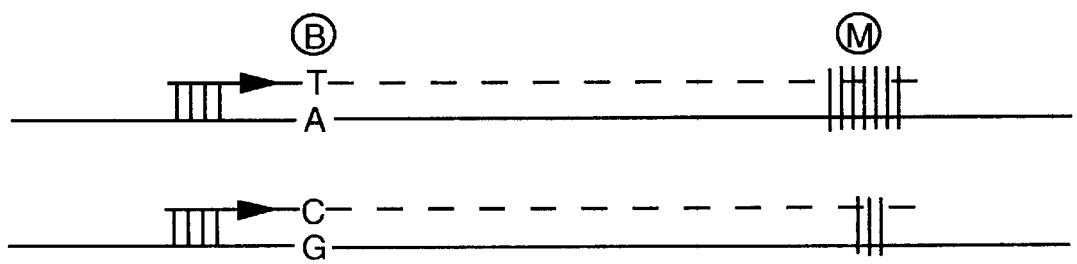
Figure 3:
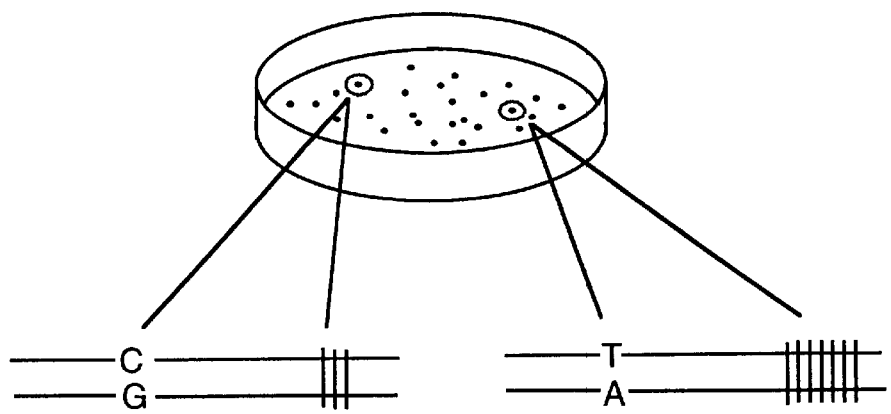

This exonuclease-based method generates selected loci from whole genome samples by selective protection of the desired locus from exonuclease hydrolysis. See FIG. 3 for a detailed schematic diagram of this method. A primer is designed to flank the locus. The genomic DNA is denatured and the primer allowed to anneal to its target by lowering the temperature. After annealing, the primer is extended at least once with a thermostable DNA polymerase at 72° C., generating a double-stranded allele-specific extension product. DNA strands without the primer annealing sequence remain single stranded. Treatment with the exonuclease degrades single-stranded DNA while double-stranded DNA remains intact. If the extension product reaches a distal variable site (the M locus in FIG. 3), the variable site (the M allele in FIG. 3) is protected. The protected extension products are cloned into a vector to create an anthology. Genotyping of individual clones may then be performed by any of several known methods for the distal variable site with the expectation that only a single allele will be found. The result of the assay is thus a genotype at the B and M loci as well as the unequivocal haplotypes for the combination.

In an alternative method for generating genome anthologies one may use affinity capture techniques. In this embodiment, genomic DNA from an individual is digested by restriction enzyme (for example, an infrequently cutting enzyme-8 bp cutter or larger, or methylation sensitive, etc.) and applied to an affinity matrix at a specific temperature and annealing buffer composition. The affinity matrix may consist of a specific DNA oligonucleotide that anneals to the target site in the genomic DNA. Non-binding genomic DNA is washed away leaving the target sequence attached to the matrix. The target sequence is then eluted from the matrix and collected. This material represents both strands of the target sequence. The collected material may be cloned for preservation purposes, not necessarily for accumulation of quantities or isolation of molecules.

In a similar method, the oligonucleotide is labelled with a biotin moiety, annealed to the genomic DNA target, and applied to a streptavidin affinity matrix. Biotin/streptavidin is an obvious example; other combinations should be possible.

Instead of DNA oligonucleotides, the targeting may consist of Peptide Nucleic Acids (PNA). PNAs are DNA analogs with the sugar/phosphate backbone replaced by a peptide-like backbone. PNA/DNA duplexes have a higher dissociation temperature than DNA/DNA or DNA/RNA, allowing greater stringency for specificity in annealing and purification conditions.

In one embodiment of the present invention, normal genotypic variation is correlated with subtle phenotypic changes, and the variation found is utilized for diagnosis and therapeutics (i.e., pharmacogenomics). By providing clones which can be efficiently manipulated in a number of ways and with different techniques, the present invention provides sufficient material for a variety of tasks over long periods of time. Inherent variation along with unambiguous phase information at any site within the locus is discoverable and identifiable, without contamination or interaction with other regions.

In another embodiment of the present invention, natural gene variants are harvested to generate a genome anthology. DNA from individuals is extracted and collected in a genome anthology for a given locus which can be utilized in the pharmaceutical development process. Each of the gene variants is a naturally occurring product that can then be manipulated as a target for pharmaceutical development.

Another embodiment of the present invention relates to the expression of the gene variants to obtain the protein products that correlate with the genes in an expression system. The variants of the gene, now manifested as isoforms, have different properties, either in catalysis, agonist binding, or target adhesion, as well as general structural properties which renders them specific targets for pharmaceutical development.

In yet another embodiment, the gene variants are cloned in reporter systems. The reporter is then utilized to monitor the expression of the gene variant. Different gene variants may be correlated to variable expression levels, and not to the structure of the protein product itself. Therefore, the gene variants in the anthology may also comprise collections of variable regulatory sequences, enhancers, and promoters that may be of importance in pharmaceutical developments. For instance, different gene variants may respond to a given suppressor compound in different ways. Some cell-lines containing gene-variants are hypersensitive to the suppressor and may be known to be down-regulated, whereas all lines with less sensitive variants will continue expression levels close to normal.

Any gene or genomic locus may be targeted for a genome anthology. Typically, the locus selected may be up to 300 kb in size. However, locus of greater than 300 kb are also possible. The criterion for selecting a locus will vary from one anthology to the next. Below, several example target regions are set forth. These examples are not intended to limit the scope of the present invention but rather serve as illustrative examples of regions which can be selected. The skilled artisan will recognize that any locus may be targeted for a genome anthology and hence is encompassed by the present invention.

All publications, patents and articles referred to within the specification are herewith incorporated in toto, by reference into the application. The following examples are presented to illustrate the present invention but are in no way to be construed as limitations on the scope of the invention. One skilled in the art will readily recognize other permutations within the purview of the invention.

EXAMPLE 1
Yeast Spheroolast Transformation

Yeast spheroplast transformation was accomplished using Y724 strain. A 10 ml, overnight culture was prepared using a single colony of yeast strain Y724 (Bradshaw et al. 1995), (Mat α, ura3-52, lys2-801, ade2-101, trp1-Δ1, leu2-Δ98, his 3-Δ200, cyh$^r$, can 1$^r$) in YPAD liquid medium (yeast extract, peptone, adenine, dextrose). The YPAD medium (50 mls) was inoculated with 5 ml of overnight culture ($OD_{600}$ approximately 1.0–1.5). Incubation with shaking at 30° C. for 4 to 4.5 hrs produced a final $OD_{600}$ of about 4.0. The cells were collected by centrifugation (5 min, 400–600×g or 2200 RPM in a table top centrifuge), rinsed once with 20 ml water and once with 20 ml of 1 M sorbitol and the cells resuspended in 20 ml of SPEM (1 M sorbitol; 10 mM sodium phosphate, pH 7.5; 10 mM EDTA; 30 mM 2-mercaptoethanol (42 μl to 20 ml SPE added just before use)). The cells were incubated for 10 min at room temperature, and 8 μl of 10 mg/ml zymolyase 100T (obtained from Saikagaku, prepared in TE with 5% glucose as suggested by the manufacturer, aliquoted and stored at −70° C.) was added followed by incubation at 30° C. for 15 min. The spheroplasts were collected by gentle centrifugation for 6 mi at 200–300×g (1200 RPM in table top centrifuge), rinsed once with STC (1 M sorbitol; 10 mM Tris; pH 7.5: 10 mM $CaCl_2$), and resuspended in 2 ml STC. Linearized vector and target DNA at a molar ratio of 1:16 totaling 5 μg were added to 15 ml round bottom falcon tubes followed by the addition of 450 μl of cells to each tube with gentle mixing and incubation for 10 min at room temperature. Equal volumes of PEG Part I (PEG 8000 Sigma 40% W/V) with PEG Part II (20 mM Tris pH 7.5, 10 mM $CaCl_2$) were mixed and 3 ml of the PEG mixture was added to each tube and gently mixed by inversion followed by incubation for an additional 10 min at room temperature.

The samples were centrifuged at 200–300×g for 6 min (1200 RPM in table top centrifuge, the PEG removed by vacuum suction and the pelleted spheroplasts resuspended in 450 μl of SOS liquid medium (1 M sorbitol; 6.5 mM $CaCl_2$; 0.25% yeast extract; 0.5% peptone; 10 μg/ml leucine or leucine and uracil depending on the selectable marker). The samples were then incubated at 30° C. for 40 min without shaking. The settled spheroplasts were gently resuspended and 150 to 300 μl of the spheroplasts were mixed with 8 ml of -Leu or -Leu/Ura top agar maintained at 46° C. and poured onto -Leu or -Leu/Ura SORB plates to select for transformants. The plates were incubated at 30° C. for 3–5 days and the colonies analyzed by colony PCR using appropriate primers.

EXAMPLE 2

Figure 4A:
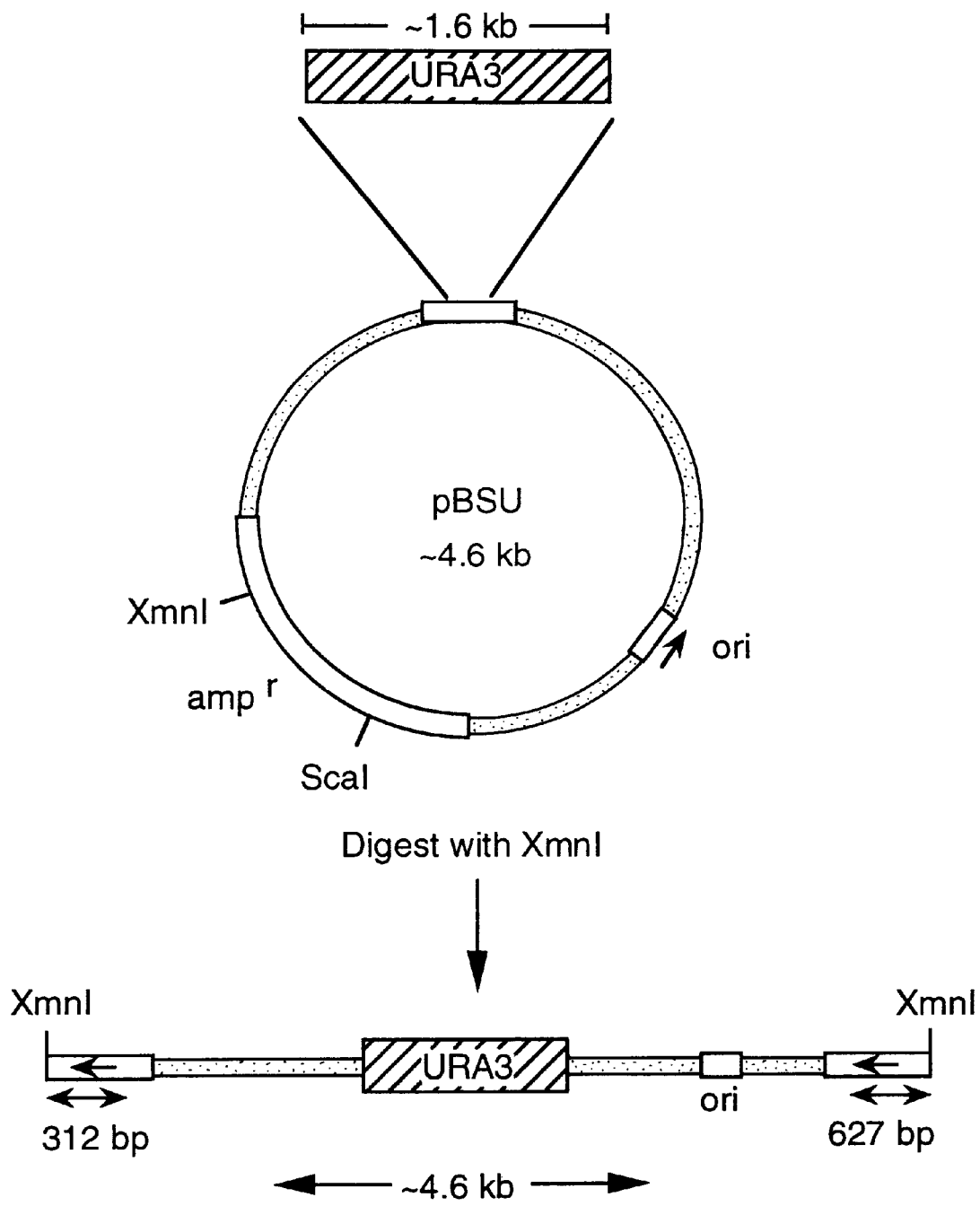
FIGS. 4A–4C Monitor cassette for optimizing yeast transformation. The URA3 gene is the target for pClasper equipped with recombinogenic ends complementing the vector backbone. The recombinogenic sequences correspond to sequences of 321 and 627 base pairs flanking the unique XmnI site in the ampicillin resistance gene of pBluescript. Linearization of the plasmid with XmnI exposes the recombinogenic sites for targeting by Clasper. (B) Construction of Clasper recovery vector. The Clasper recovery vector for the URA3 monitor cassette was constructed by cloning PCR products amplified from the pBluescript vector into pClasper. Linearization of Clasper at a unique NruI site between the recombinogenic ends prepares Clasper for recovery of the monitor. (C) Recombination between monitor cassette and Clasper. Linearized Clasper (pClSX) and monitor (pBSU) are mixed and presented to the yeast spheroplasts during the co-transformation event. Recombination takes place between the homologous DNA sequences of pBSU and pClSX. Only recombinants are able to grow on selection medium lacking leucine and uracil.
Figure 4B:
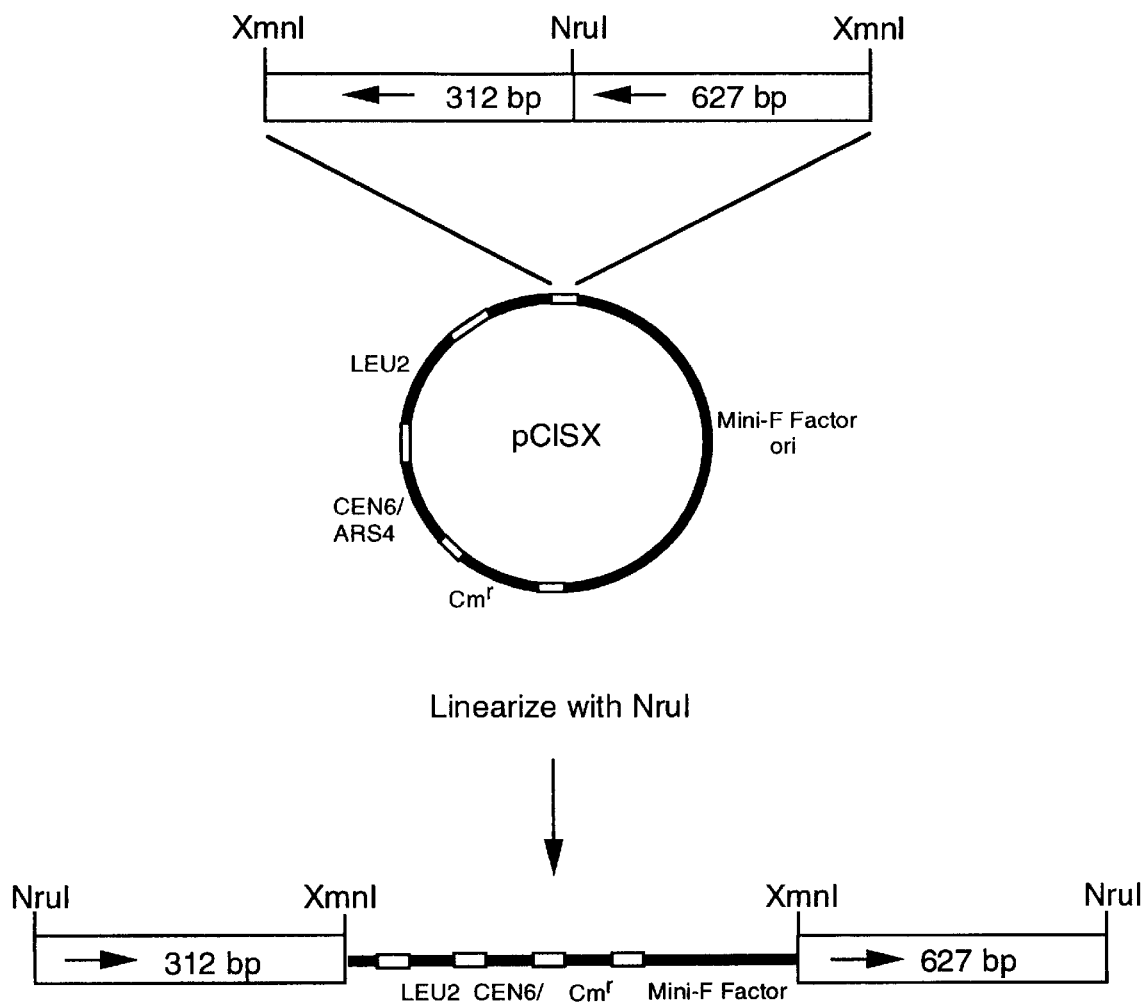

An example of a model system for optimizing yeast co-transformation methods is the URA3 Target Monitoring system. Construction of this model system was performed as follows. The gene for URA3 (1.55 kb), a yeast selectable marker, was inserted at the XbaI site of the multiple cloning region of the bacterial plasmid vector, pBluescript (FIG. 4A). Within the vector backbone, a unique restriction site, XmnI, was identified in the ampicillin resistance gene. The vector containing the URA3 gene, hereinafter called the target monitor (pBSU), is linearized by digestion with XmnI so that vector sequences immediately adjacent to the XmnI site are exposed for recombination with pClasper. From the vector sequence immediately flanking the XmnI site, oligonucleotide primers were designed and synthesized to amplify sequence from the vector by PCR. The primers were designed with restriction enzyme recognition sites on their 5' ends for ease of cloning the amplicons into pClasper (see primers below). Primers LZU1F and LZU1R amplified a 627 bp sequence downstream from the XmnI site. Primers LZU2F and LZU2R-S amplify a 312 bp sequence upstream of the XmnI site. The amplified vector sequences were cloned into pClasper such that the sequences were joined at the NruI sites on the 5' ends of LZU1R and LZU2F (FIG. 4B). The pClasper construct (pC1SX) and the target monitor (pBSU) were prepared for co-transformation by linearizing the circular plasmids with NruI (for pC1SX) and XmnI (for pBSU).

Figure 4C:
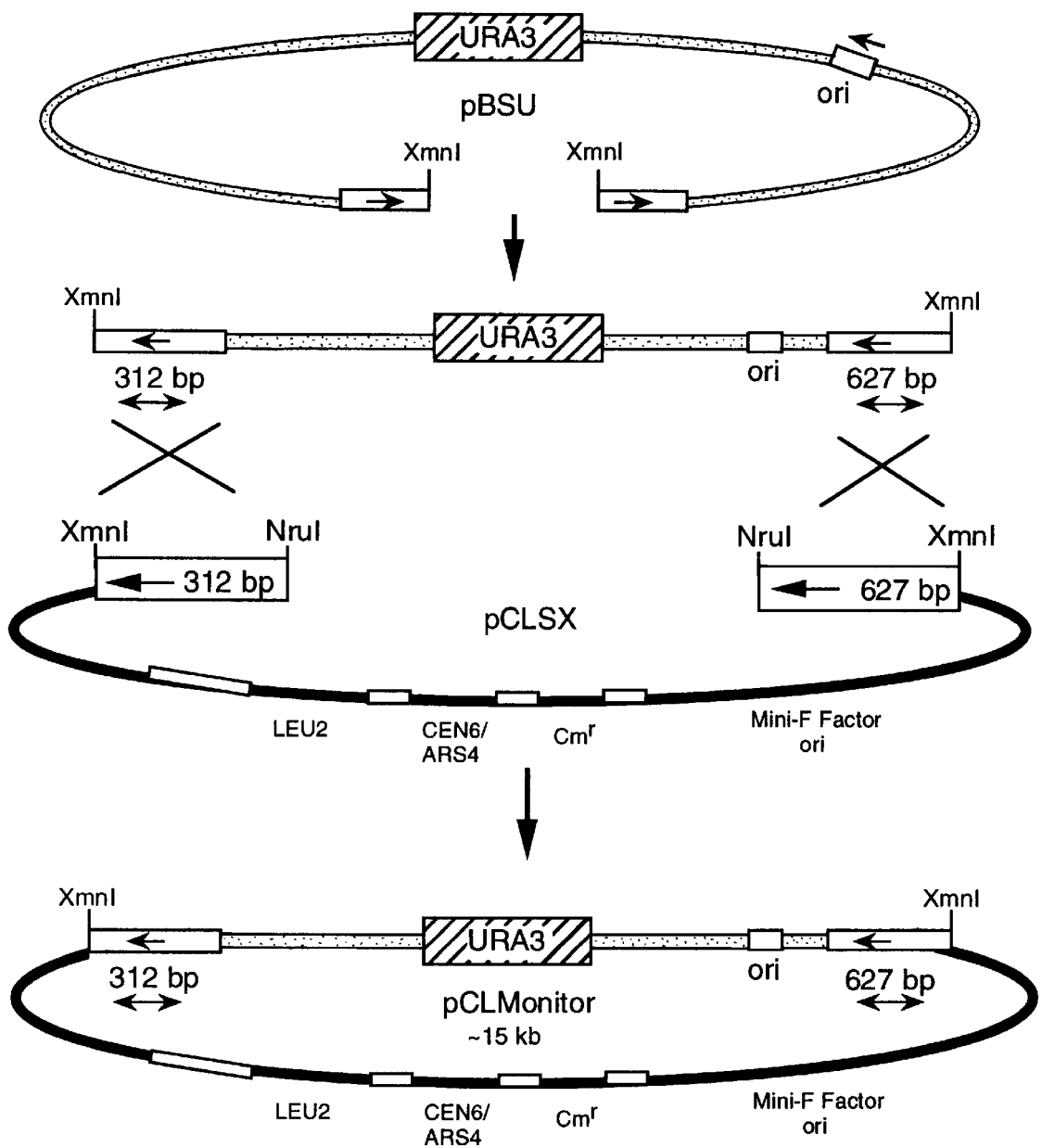

A protocol for optimizing co-transformations of yeast follows. The linearized PBSU and PCLSX were mixed and presented to spheroplasts of yeast strain Y724 that is auxotrophic for endogenous URA3 and LEU2. Recombination between pClSX and pBSU occurred in vivo, resulting in a recombinant, pClSXURA3, containing the entire PBSU and pClSX (FIG. 4C). Transformed yeast cells were plated for growth on selection medium lacking uracil and leucine. Only yeast cells containing the correct recombinant, pClSXURA3, will grown on the selection medium.

Using the URA3 target monitoring system, the yeast spheroplast transformation method of Burgers and Percival (1987) was used as the initial protocol and optimized to the method described in Example 1. In the first experiments designed to optimize the co-transformation procedures to obtain high frequencies of transformants, spheroplasts are transformed with the target monitor system as a simple mixture of pBSU and pClSX. Protocol variables were optimized and standardized. Once an efficient transformation protocol was achieved, native uncloned genomic DNA was added to the pBSU and pClSX mixture and TIVC was used to rescue single copy targets from genomic DNA.

The following parameters were found to significantly increased transformation efficiency and absolute numbers of transformants: cell number for spheroplasting ($10^8$ cells/ml), cell number for transformation (1–2×$10^9$ cells/ml), Zymolyase concentration (3–4 units/ml cells), Zymolyase purity (100T>20T), source of Zymolyase (Saikagaku 100T>ICN 20T>Saikagaku 20T), and vector (pClSX):target (pBSU) molar ratio (1:16).

Figure 5:
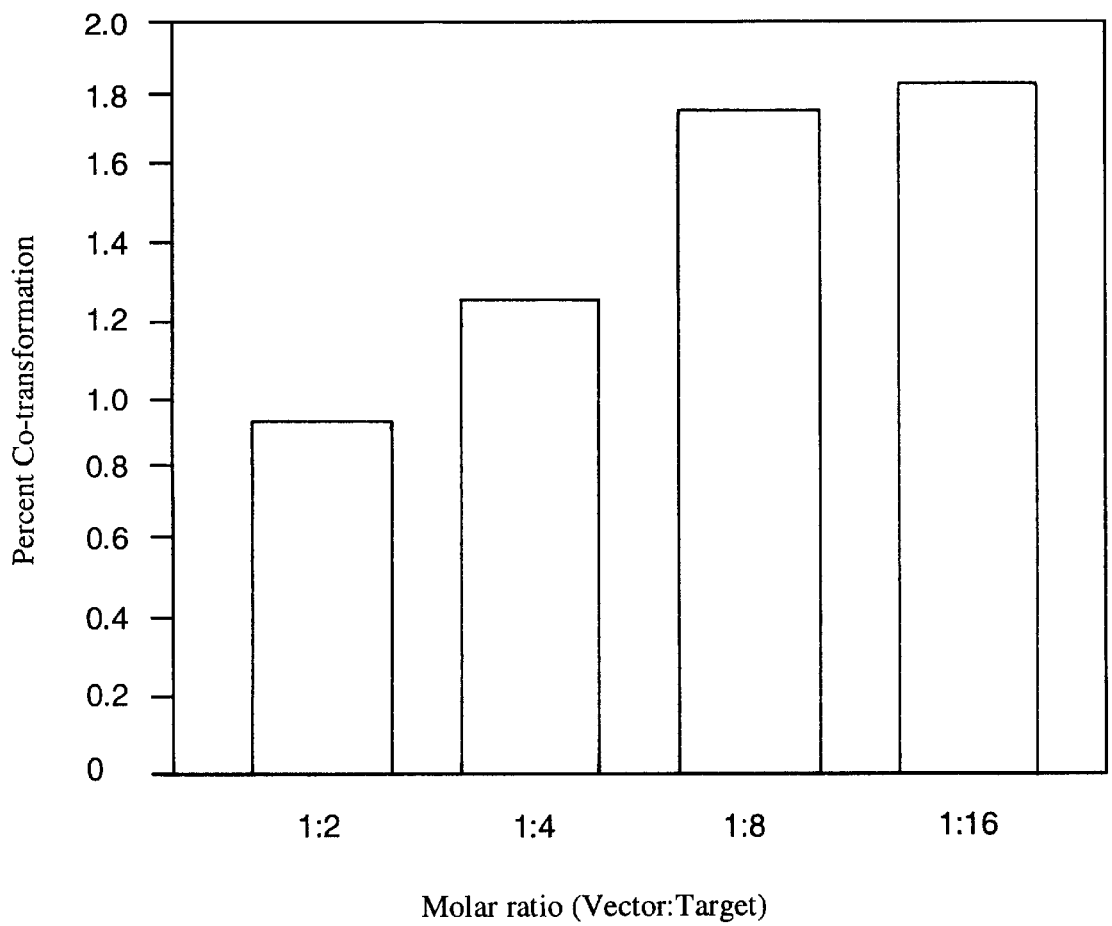
FIG. 5. Effect of vector:target molar ratio on co-transformation efficiency. Yeast cells were co-transformed in parallel experiments with pClSX (vector) and pBSU (target monitor) using molar ratios as given, starting with 1 μg of pBSU. All transformations were performed in triplicate. Optimal vector:target molar ratios for co-transformations were in the range of 1:8 to 1:16.

Using these optimized parameters, co-transformations consistently yield in the range of $10^6$ transformants/μg of DNA. FIG. 5 illustrates the effect of vector:target molar ratio on co-transformation efficiency. In this experiment, performed in triplicate, pBSU was held constant at a mass of 1 μg PBSU, while the mass of the vector, pClSX, was reduced to achieve the indicated ratios. Control transformations were performed consisting of transforming yeast with either the linearized pClSX or the linearized pBSU alone. The highest transformation efficiency was found in the range of 1:8 to 1:16. No colonies were observed on the control plates as expected. Based on the number of spheroplasts used for each transformation ($10^8$), a 2% co-transformation efficiency equals 2×$10^6$ transformants. This result indicates that conditions for high frequency recovery of recombinants have been achieved for simple co-transformations of yeast with a vector and a cloned target.

Figure 6:
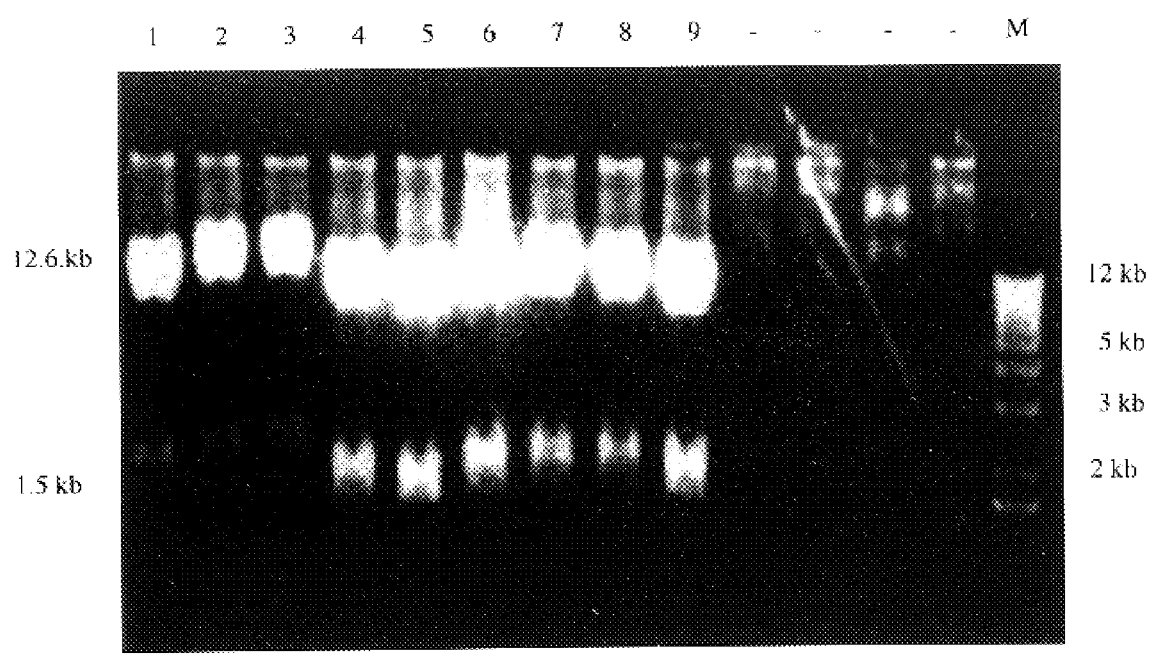
FIG. 6. XbaI restriction enzyme digestion of pClSXURA3 recombinants shuttled from yeast to bacteria. DNAs from nine pClSXURA3 yeast recombinants were shuttled to bacteria by electroporation. Plasmid DNA from bacterial tranformants, each representing one of the nine original yeast recombinants, were digested with XbaI to release the 1.5 kb URA3 gene from the remaining 12.6 kb pClSXURA3 recombinant. "–" means non-recombinants from control plates; "M" indicates size marker.

In another experiment using a pClSX:pBSU molar ratio of 1:16 for a total mass of 1 μg DNA, approximately 8×$10^5$ leu$^-$/ura$^-$ transformants were observed on plates containing yeast transformed with the pClSX/pBSU mixture when the optimized co-transformation protocol from Example 1 was used. To confirm that the yeast colonies grown on the leu$^-$/ura$^-$ selection medium contained pClSXURA3 recombinants, ten recombinant colonies were picked, total yeast DNA was prepared, and transferred to bacteria by electroporation. Transfected bacteria were selected on LB medium supplemented with 20 μg/ml chloramphenicol, and plasmid DNA was purified for analysis by restriction endonuclease digestion. FIG. 6 shows the XbaI restriction endonuclease pattern of pClSXBSU plasmid DNA from nine distinct bacterial colonies representing nine of the ten original leu⁻/ura⁻ yeast recombinants. XbaI digestion is expected to release the URA3 gene from pClSXBSU, resulting in two fragments of 1.5 kb (URA3) and 12.6 kb (remainder of pClSXBSU). These results confirm successful co-transformation and recombination of pBSU and pClSX in yeast, successful transfer of pClSXBSU to bacteria, and stable growth and faithful replication of pClSXBSU in both yeast and bacteria.

Figure 7:
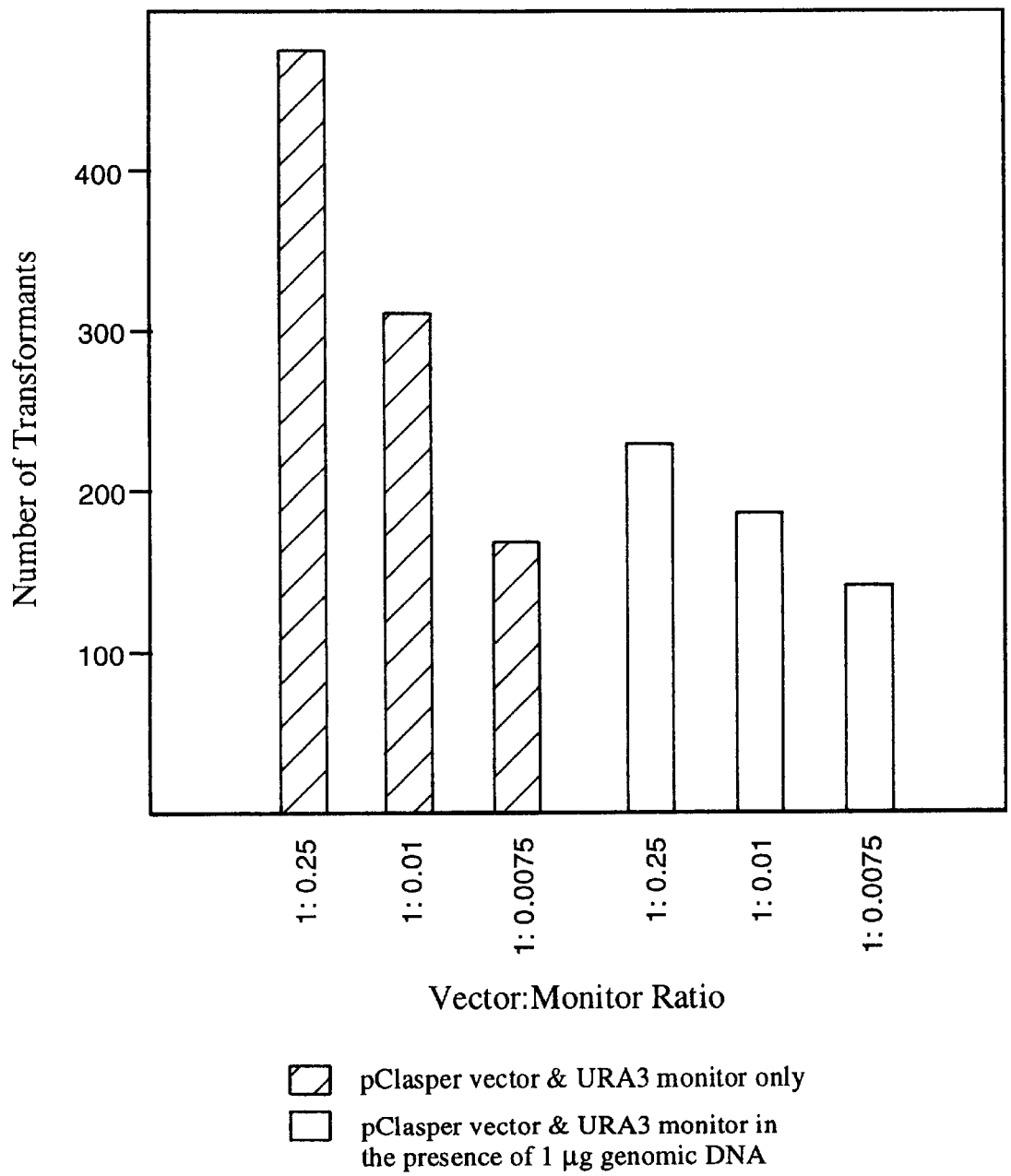
FIG. 7. Co-transformation of yeast strain Y724 with pClSX, PBSU, and complex mixtures of DNA. pClSX and pBSU were mixed at the molar ratios indicated and used to co-transform yeast spheroplasts in the presence and absence of 1 μg total native genomic DNA. The genomic DNA was added to illustrate rescue from a complex pool of DNA. In the experiment using a molar ratio of 1:0.0075 in the presence of genomic DNA, the target (pBSU) was present as approximately 0.1% of the total DNA used to transform the yeast spheroplasts. The result of these experiments was the successful recovery of a low copy target from a complex mixture of vector and total native genomic DNA.

In another experiment, pClSX and pBSU were mixed at molar ratios of 1:0.25, 1:0.01, and 1:0.0075, and used to co-transform yeast spheroplasts in the presence and absence of 1 μg total native genomic DNA (FIG. 7). The optimized co-transformation protocol from Example 1 was used, modified only by the ratio of vector to target and the addition of total native genomic DNA. In this experiment, the target, pBSU, was present as approximately 0.1% of the total DNA used to transform the yeast spheroplasts. As the number of copies of the target decreased, the total number of recombinants also decreased as expected. This was true for both iterations of the experiment, i.e., with and without the inclusion of total native genomic DNA. However, at the lowest molar ratio, 1:0.0075, the total number of leu⁻/ura⁻ pClSXBSU recombinants was approximately the same. The result of this experiment was the successful recovery of a low copy target from a complex mixture of vector and total native genomic DNA.

```
LZU1F    5'GTT CAT CCA TAG TTG CCT GAC 3'      BamHI
LZU1R    5'GTG CTC ATC ATT GAA AAC GTT C 3'    NruI
LZU2F    5'CGT TCT TCG GGG CGA AAA C 3'        NruI
LZURR-S  5'GCA CTT TTC GGG GAA ATG TG 3'       HindIII
```

EXAMPLE 3

Figure 8:
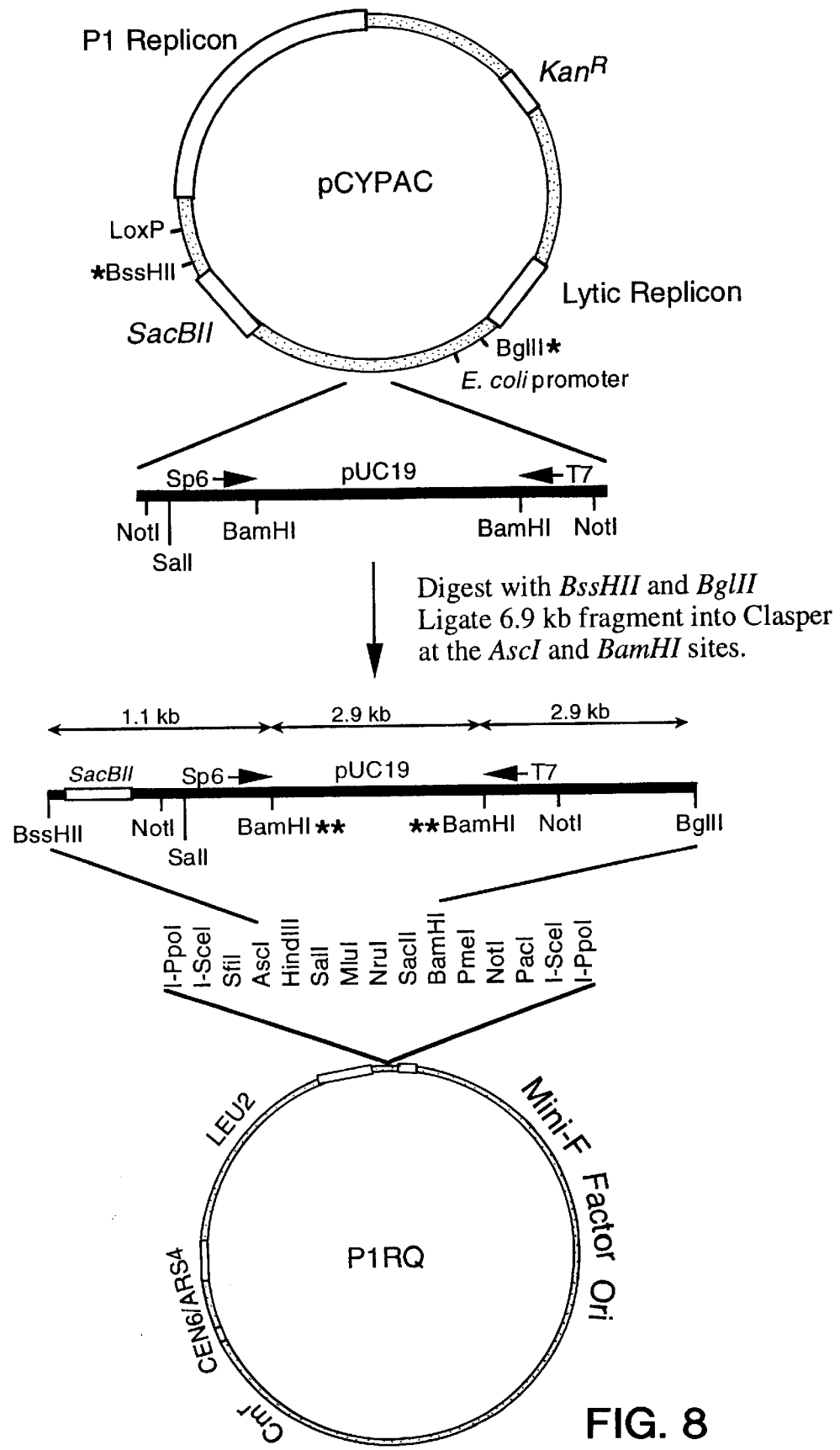
FIG. 8. Construction of a P1/PAC rescue vector (P1RQ). The P1 rescue Clasper, P1RQ, was constructed with recombinogenic sequences that target the P1 or PAC vectors adjacent to the cloned insert. The pCYPAC vector was digested with BglII and BssHII (*), releasing a 7 kb fragment containing the BamHI cloning site, T7 and Sp6 promoter recognition sites and the pUC19 stuffer fragment. The 7 kb BglII/BssHII fragment was cloned into pClasper at the BamHI and AscI sites. To prepare the P1RQ vector for co-transformation, the vector is digested with BamHI (**) releasing the pUC19 stuffer fragment and exposing recombinogenic ends of 1.1 and 2.9 kb in length. P1RQ can be used to rescue the entire cloned insert from any P1 or PAC library clone.

Another example of a system for in vivo cloning is the P1 Rescue Vector (FIG. 8). In this system, a pClasper vector (P1RQ) was constructed containing recombinogenic sequences from the P1 Artificial Chromosome (PAC) cloning vector, pCYPAC (Ioannou, et al., 1994). The purpose of P1RQ is to rescue the DNA insert from genomic clones of P1 and PAC libraries. The PCYPAC sequences that are the recombinogenic targets for P1RQ are located in the vector regions flanking the insert. Because it uses recombinogenic target sequences common to all PAC clones, P1RQ can rescue the insert from any PAC clone. Additionally, since the targeted region of the PAC cloning vector is identical to that of the vector for the P1 cloning system, pAD10SacBII (Sternberg, 1990), the insert from any P1 library clone can also be rescued.

P1RQ was constructed by digesting the PAC vector with BglII and BssHII (FIG. 8, single asterisks). This releases a 7 kb BssHII/BglII fragment containing the BamHI cloning site of the vector, the Sp6 and T7 promoter recognition sequences, and the pUC19 stuffer fragment that is substituted with genomic DNA during cloning. The 7 kb fragment was cloned into pClasper at the BamHI and AscI sites, as these sites are compatible with BglII and BssHII, respectively. To prepare the P1RQ vector for co-transformation, the vector is digested with BamHI and SalI (FIG. 8, double asterisks) releasing the pUC19 stuffer fragment and exposing the recombinogenic ends that are 1.1 and 2.9 kb in length. The linearized P1RQ and the P1 or PAC clone to be rescued are then used to co-transform yeast cells. Note that the P1 or PAC genomic clone target is circular, and does not require linearization prior to transformation of yeast. Recombination occurs between the linearized P1RQ vector and the circular genomic P1 or PAC clone.

Figure 9A:
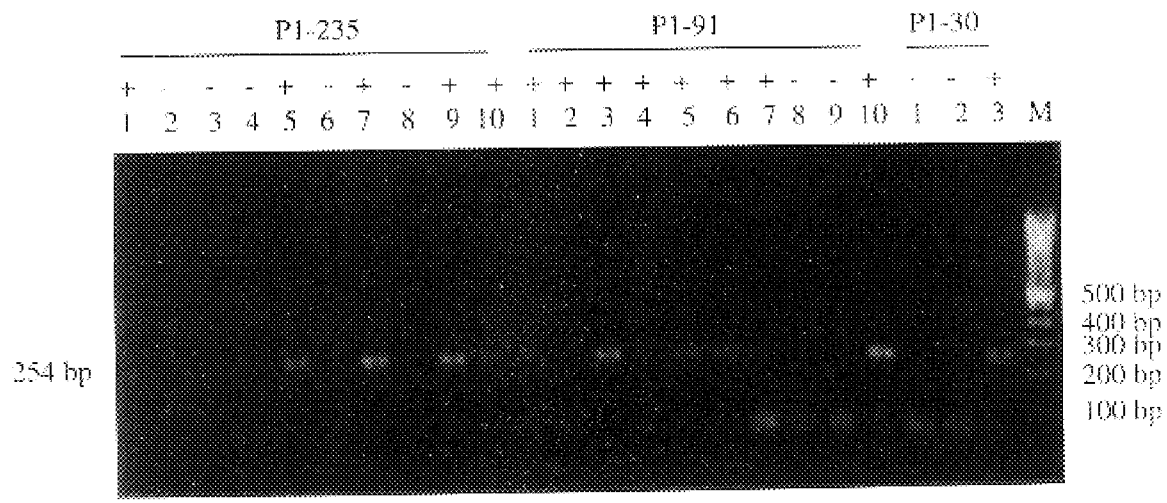
FIG. 9. Amplification products from P1 rescue Clasper (P1RQ) recombinants. Yeast spheroplasts were co-transformed with P1RQ and 4 different P1 clones containing the mouse Cdx-2 gene. Recombinants were selected on leu⁻ plates. Ten colonies from each transformation were picked and analyzed by colony PCR using primers that amplify a 254 bp region of the Cdx-2 gene. Between 50% and 80% of the colonies scored as positives indicating recombination between P1 and P1RQ. "M" means size marker; "C+" indicates PCR positive control; "C–" is a PCR negative control.
Figure 9B:
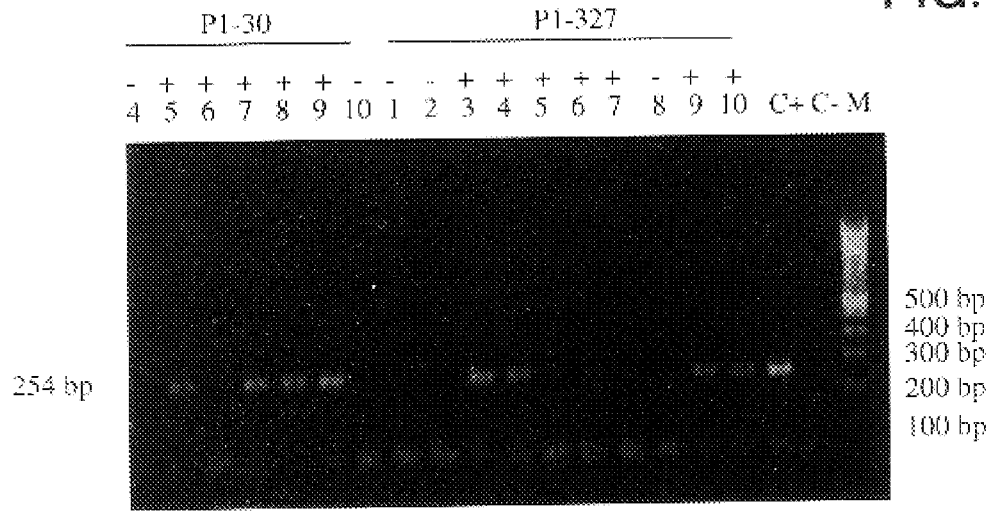
Figure 10:
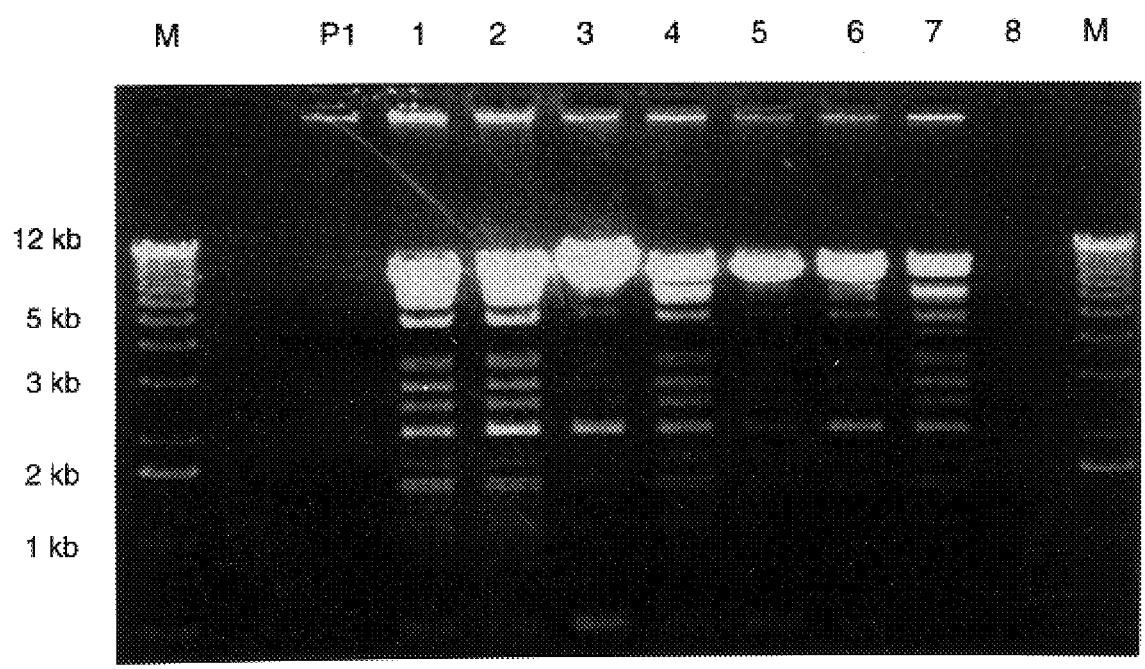
FIG. 10. EcoRI restriction enzyme digestion of P1RQ recombinants shuttled from yeast to bacteria. Seven PCR-positive recombinants were picked for transfer to bacteria. Total yeast DNA was prepared from each colony and directly used to transform E. coli strain DH10B by electroporation. Bacterial transformants were selected on LB plates containing chloramphenicol. Plasmid preps were made and the DNA was digested with EcoRI. Bacterial tranformants from the PCR-positive yeast recombinants all gave restriction patterns similar to that of the original Cdx-2 P1 (P1). The similarity in restriction patterns indicates that initial rescue in yeast followed by bacterial transformation and growth resulted in no gross rearrangements and that stable replication was accomplished. "M" is a 1 kb marker.

The P1RQ vector was used to rescue the inserts from 4 different P1 clones containing the mouse Cdx-2 gene (P1-235, P1-91, P1-170, and P1-327). The insert for each of the P1 clones was approximately 100 kb in size. The Cdx-2 locus was chosen for convenience, since four unique clones were available, and the inserts could be identified by amplifying a 254 bp product by PCR. Yeast spheroplasts were co-transformed using the protocol described in Example 1. The vector:target molar ratio was 1:16 for each co-transformation using a different P1 clone as the target. Yeast transformants were selected on medium lacking leucine. Ten yeast colonies were picked from leuselection plates for each of the P1 targets and analyzed by PCR (FIG. 9). Between 50% and 80% of the colonies picked from the selection plates were PCR-positive, indicating that recombination had occurred between the P1RQ vector and the P1 clone. To further confirm that in vivo recombination had taken place, seven positive clones were picked from the P1-327 transformation, total yeast DNA was prepared, and the P1RQ recombinants were transferred to E. coli strain, DH10B, by electroporation. Transfected bacteria were selected on LB medium supplemented with 20 μg/ml chloramphenicol, and plasmid DNA was purified for analysis by restriction endonuclease digestion. FIG. 10 shows the results from EcoRI digestion of DNAs from individual bacterial representing the seven original yeast recombinants. The EcoRI digestion pattern is the same as that for the original P1 clone (FIG. 10, lane 1). These results confirm that recombination has occurred between the P1RQ vector and the co-transforming P1-327 clone. This result also represents a second, distinct validation of the TIVC method for creating genomic anthologies, in addition to that in Example 2.

EXAMPLE 4

Figure 11:
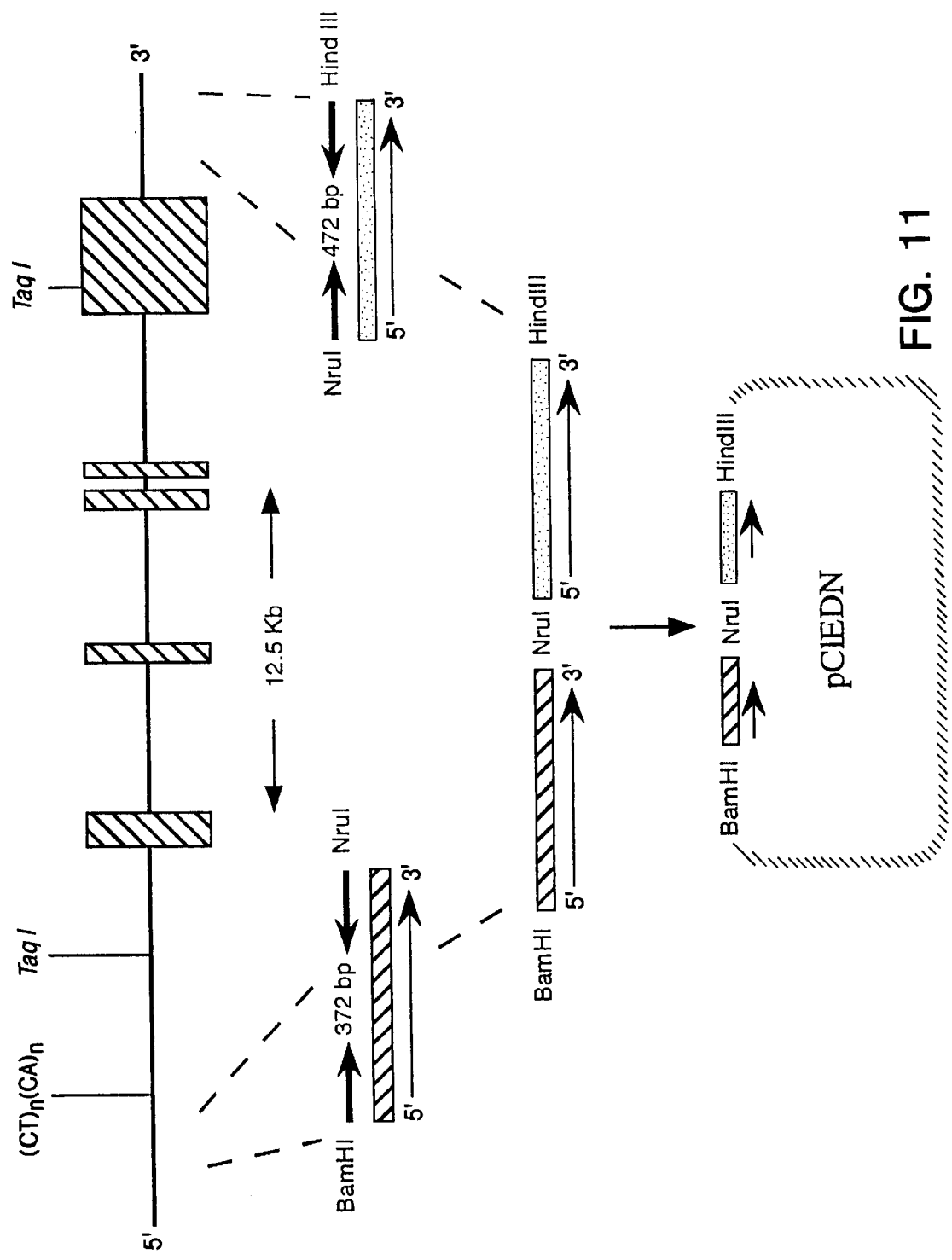
FIG. 11. Construction of a Clasper vector to generate a genome anthology for the Endothelin-1 gene. Recombinogenic ends of 372 base pairs from the 5' flanking region and 472 base pairs from the 3' flanking regions of the Endothelin-1 gene were cloned into Clasper.

One genomic region for generation of a genome anthology is the Endothelin-1 locus (FIG. 11). The Endothelin-1 (EDN1) gene is located on human chromosome 6p24-p23 and spans approximately 13 kb (Arinami et al., 1991). END1 is a member of a family of structurally and pharmacologically distinct peptides (Levin, 1995). Three members of this family have been identified in humans. END1 is a potent vasoconstrictor peptide of 21 amino acids in the mature form, that is produced by the vascular endothelial cells and also has effects on the central nervous system. END1 was chosen for genthology production for several reasons. First, as the most potent vasoconstrictor known, Endothelin-1 is the subject of intensive medical and pharmacological study in the treatment of cardiovascular disease. A genthology of Endothelin-1 provides the resource needed for a systematic analysis of variation across the entire gene and the association of the variation with cardiovascular disease. Second, the Endothelin-1 gene is of a size convenient for long-range PCR. Comparisons can be made between Endothelin-1 genthologies prepared by two different methods, long-range PCR and pClasper, to show the advantages of harvesting variants from different populations of cells or individuals.

The Endothelin-1 pClasper, pClEDN, was prepared by designing and synthesizing oligonucleotide primers that amplify recombinogenic target sequences from the 5' and 3' flanking regions of the Endothelin-1 gene (see primers below). Primers pCl-EDN5'F and pCl-EDN5'R, synthesized with recognition sequences for BamHI and NruI endonuclease, respectively, were used to amplify a 372 bp sequence from the 5' flanking region of the gene. Primers pCl-EDN3'F and pCl-ECN3'R, synthesized with recognition sequences for NruI and HindIII, respectively, were used to amplify a 472 bp sequence from the 3' flanking region of the gene. The amplified sequences were digested with the appropriate enzymes and cloned into pClasper in a head-to-tail manner. The completed pClEDN vector was linearized with NruI prior to co-transformation of yeast with uncloned, native genomic DNA.

Figure 12:
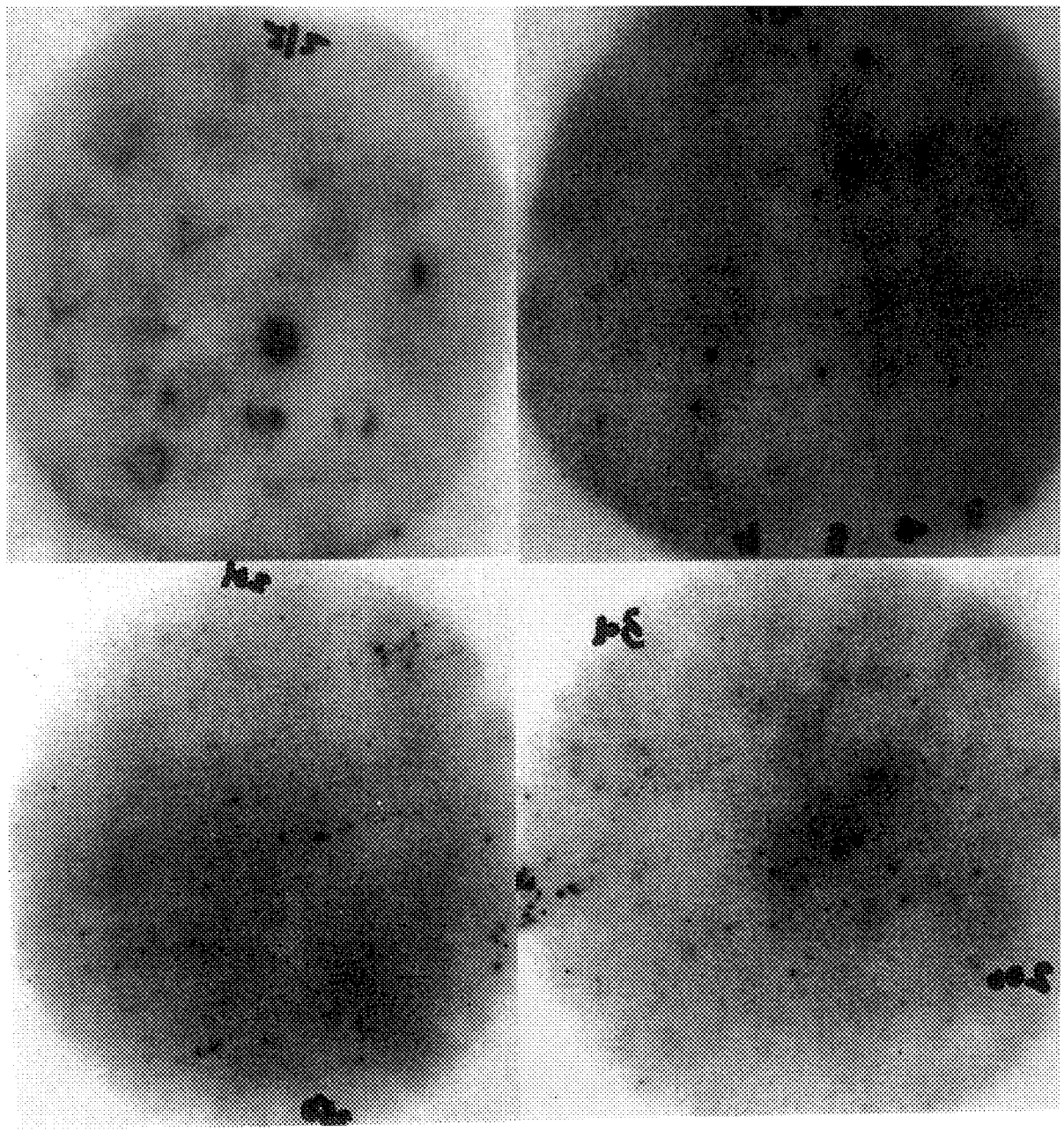
FIG. 12. Colony hybridization of pClEDN transformants. A probe was prepared by amplifying and radiolabeling a ~500 bp fragment from exon 2 of the Endothelin-1 gene using total human genomic DNA as a template. Filters were hybridized at 65° C. and washed to a final stringency of 0.2× SSC, 0.1% SDS at 55° C.

Parallel experiments were performed to harvest the EDN1 gene from individual DNAs of CEPH family 13294, and a pool prepared by mixing the DNAs of all members of the family. Family 13294 DNAs were prepared as described in Example 7. The co-transformation protocol described in Example 1 was used with the following modifications. The pClEDN Clasper vector (FIG. 11) and total native genomic DNA were mixed at ratios of 1:5 and 1:10. When agarose-embedded DNAs were used, the agarose blocks were melted at 70° C., pooled, and mixed gently with the vector at the appropriate ratio. The mixture was cooled to 37° C. and incubated for 2 hrs with β-agarase prior to co-transformation of yeast spheroplasts. For genomic DNAs not embedded in agarose, the vector and genomic DNA were mixed and incubated at 70° C. for 2 minutes, followed by incubation at 37° C. for 2 hr. Transformants were selected on medium lacking leucine. Transformants were analyzed by colony hybridization on filters prepared from the selection plates. The filters were lifted from the plate and autoclaved for 10 minutes (with a 10 min. drying cycle), washed with 2× SSC, and prehybridized in hybridization solution for one hour at 65° C. A 500 bp probe was amplified from the second exon of the Endothelin-1 gene using total human genomic DNA as a template. The amplicon was used as the template in a PCR radiolabeling procedure using the exon 2 primers and incorporating $^{32}$P-dCTP. Filters were hybridized at 65° C. overnight and washed to a final stringency of 0.2× SSC, 0.1% SDS at 55° C. FIG. 12 illustrates autoradiographs of the colony hybridization results from co-transformant plates.

tion pathway eventually resulting in contraction of the blood vessel. The ENDRA gene was chosen for genthology generation for the following reasons. ENDRA is the receptor for Endothelin-1, a locus chosen for the first genthology (Example 4), and is a pharmacological target for drugs that block the vasoconstriction activity in Endothelin in treatment in hypertension. An ENDRA genthology is used for genotyping to screen individuals for sensitivities to these drugs. Secondly, the ENDRA locus is approximately 40 kb in size and represents a moderately-sized gene for generating a genthology.

The ENDRA pClasper, pC1ENDRA, was constructed by designing and synthesizing oligonucleotide primers from sequences in the 5' and 3' flanking regions of the ENDRA gene (see primers below). Primers ENDRA5'F and ENDRA5'R were synthesized with recognition sequences for HindIII and MluI, respectively, at their 5' ends. This set of primers amplifies a 520 bp sequence from the 5' flanking region of the ENDRA gene. Primers ENDRA3'F and ENDRA3'R were synthesized with recognition sequences for BamHI and NotI, respectively, at their 5' ends. This set of primers amplifies a 568 bp sequence from the 3' flanking region of the ENDRA gene. The amplified sequences were digested with the appropriate enzymes and cloned into pClasper in a head-to-tail manner. The completed pC1ENDRA vector was linearized with BamHI and MluI prior to co-transformation of yeast with uncloned, native genomic DNA.

```
ENDRA5'F    nt 17-37      5'GCT ACA TGG AGC AAA AAC-        HindIII
                            GAG 3'
ENDRA5'R    nt 518-537    5'TAC TGG ATC AGG TGG TTT GC 3'   MluI
ENDRA3'R    nt 2011-2030  5'CTT CGC CAG ACA GAT TGC TG 3'   BamHI
ENDRA3'F    nt 2558-2579  5'ATA TTA CTA AGG AGA G-          NotI
                            GT TTG C 3'
```

Figure 13A:
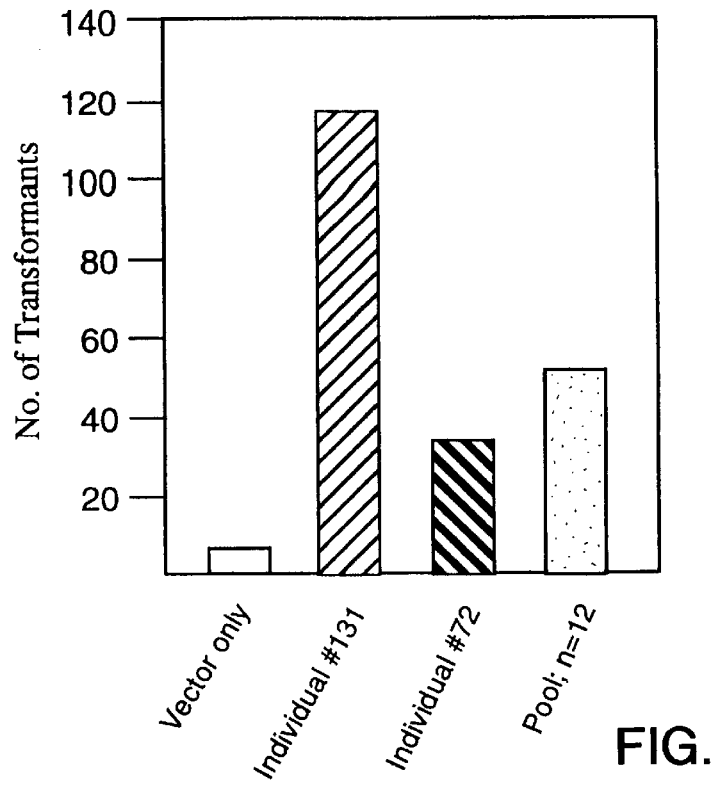
FIGS. 13A–13B. (A) Co-transformation with pClEDN and individual or pooled DNAs. Yeast were co-transformed with pClEDN and native genomic DNA from individuals and pooled members of Family 13294. Each bar represents a co-transformation experiment performed in triplicate and indicate the DNAs giving the highest (individual #131) and lowest (individual #72) number of transformants when used alone. This is compared with the number of transformants using pooled DNA from individuals. (B) Co-transformation with Hoxc8 Claspers and genomic DNA from transgenic mice. Each bar represents triplicate iterations of co-transformations with either pClC8-18 kb or pClC8-21 kb and genomic DNA from transgenic mice carrying the lacZ-URA3 reporter construct.

FIG. 13A shows a graph indicating the number of co-transformants from experiments (performed in triplicate) using single individuals from Family 13294 and a pool of all members of the family. When compared to the control plates in which only linearized vector was used, the number of co-transformants from uncloned native genomic DNA was between 4- and 12-fold greater. These results confirm the capability of using TIVC to create a genome anthology for a specific locus from individual and pooled uncloned native genomic DNAs.

EXAMPLE 6

Figure 15:
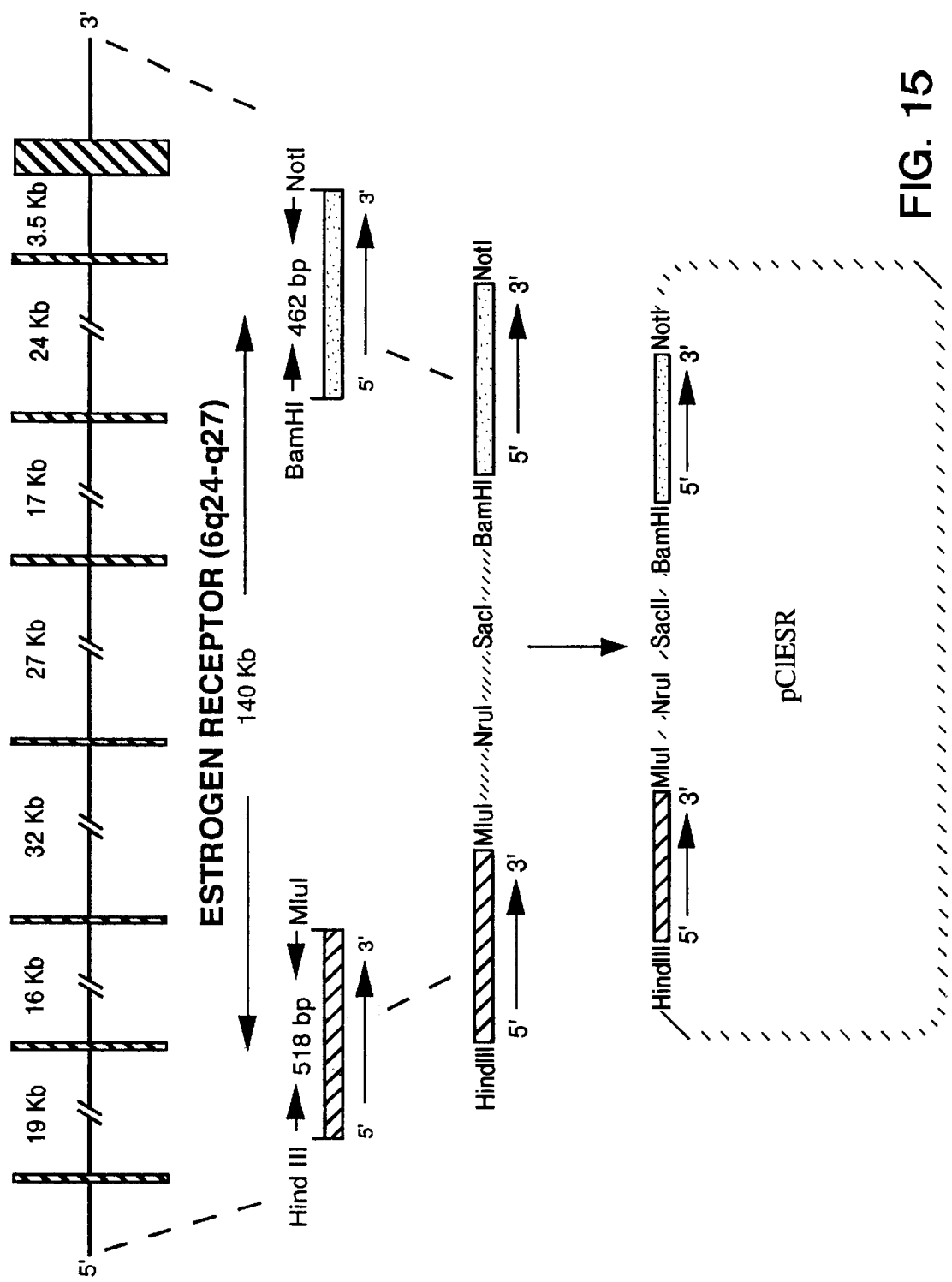
FIG. 15. Construction of Estrogen receptor Clasper. pClESR was constructed using recombinogenic ends of 518 and 462 bp, from the 5' and 3' flanking regions, respectively, of the Estrogen receptor gene.

Another genomic region used to illustrate the generation of a genome anthology is the Estrogen receptor α(ERα) locus on human chromosome 6q24-q27 (FIG. 15). The gene spans approximately 140 kb (Ponglikitmongkol et al., 1988). ERα is a member of the nuclear hormone receptor super-family that includes receptors for various other steroids, retinoids, thyroid and vitamin D (McDonnel et al., 1993). A second estrogen receptor, ERβ has recently been identified (Kuiper et al., 1996; Mosselman et al., 1996). The ER has distinct domains for ligand binding and for DNA binding.

```
pCL-EDN5'F    nt 501-521   GTG ACT GTG GCC AAA AGG AGC      BamHI
pCL-EDN5'R    nt 853-873   TGG CAC CTG CCT TCT CTG TCC      NruI
pCL-EDN3'F    nt 532-555   TTC TTC GTG ATA GCC TAG GAC TG   NruI
pCL-EDN3'R    nt 982-1004  CAG AGT CAC GCA CTG AGA AAA AG   HindIII
```

EXAMPLE 5

Figure 14:
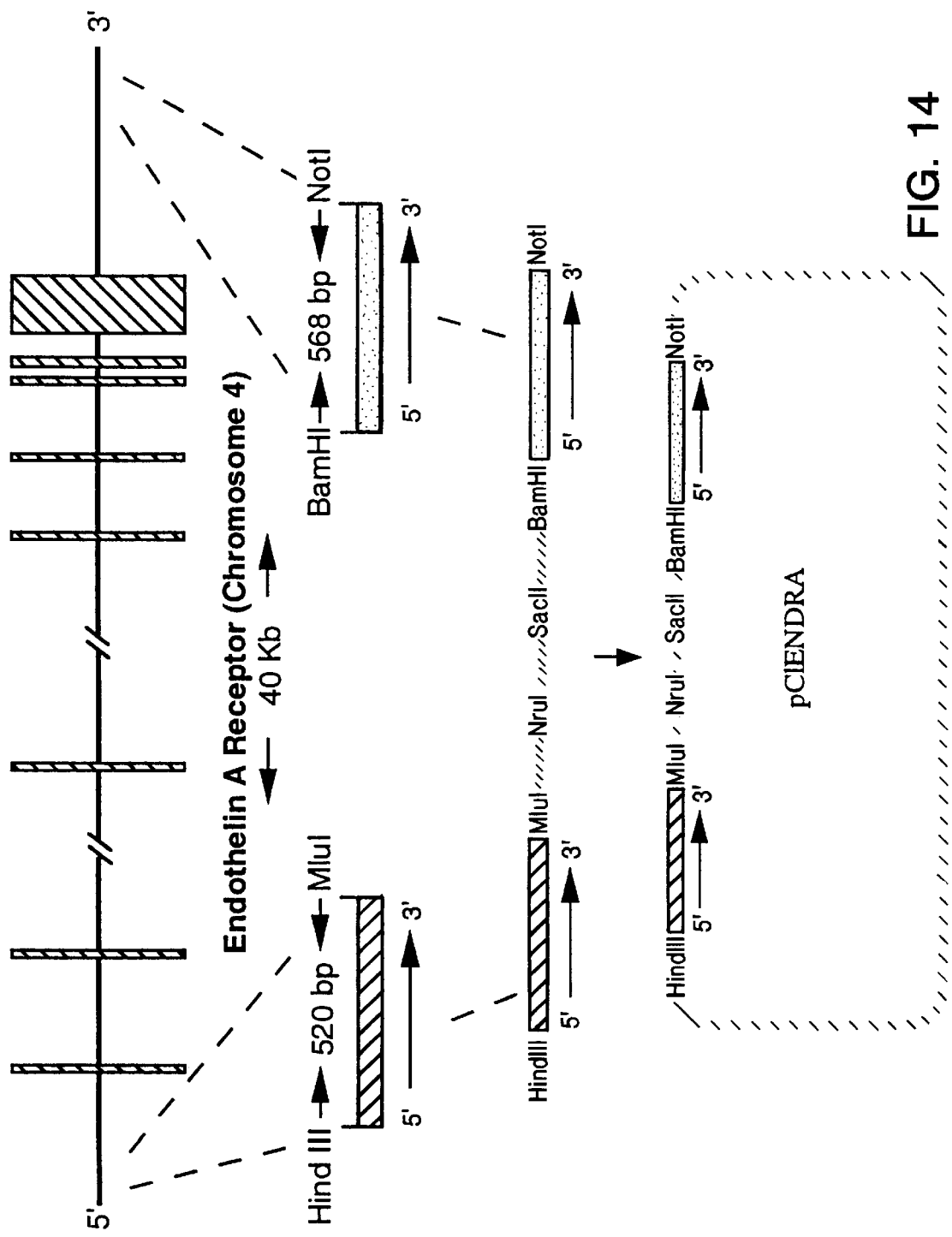
FIG. 14. Construction of Endothelin A receptor Clasper. pClENDRA was constructed using recombinogenic ends of 520 and 568 bp, from the 5' and 3' flanking regions, respectively, of the Endothelin A receptor gene.

A second genomic region for a genome anthology is the Endothelin receptor A (ENDRA) locus on human chromosome 4 (FIG. 14) (Hosoda et al., 1992). The gene spans approximately 40 kb. ENDRA is one of the two known members of the Endothelin receptor family that are the cell-surface binding sites for the Endothelin peptides (Hosoda et al., 1992; Arai et al., 1993). Endothelin receptors are members of the super-family of seven transmembrane domain, G-protein coupled receptors (Adachi et al., 1993). ENDRA is primarily expressed on the surface of vascular smooth muscle cells, where it binds the vasoconstrictor peptide, Endothelin-1. The receptor transmits a message through the cell membrane to the G-protein signal transduc- The ER transduces signals to its target genes by at least two pathways. The major pathway involves the binding of the ligand, estrogen, that has entered the cell by passive diffusion. Binding of the ligand and ER may occur in the cytoplasm or nucleus. Ligand binding displaces chaperon proteins from the ER by a conformational change that ultimately leads to the formation of an ER homodimer carrying the ligand. The dimerized receptor-ligand complex then binds to specific steroid response elements in the promoter regions of Estrogen responsive target genes. The DNA bound receptor-ligand complex then interacts, either directly or indirectly via specialized adaptor proteins, with the transcription apparatus of the target gene. Either positive or negative effects are imposed on the expression of the target gene, depending on the cell-, promoter-, or adaptor protein-context of the gene and bound receptor complex. ER was chosen because it is a major subject of research in medicine and pharmacology due to its role in cancer, cardiovascular disease, and osteoporosis. There is a wealth of data on somatic mutation, polymorphism, expression variation, and individual response to drugs, although no systematic attempt has been made to correlate genotypic variation with phenotype. Finally, at 140 kb in size, the ERα locus provides a target for creating a genome anthology that could not be done with other current methods of whole gene analysis.

The ER pClasper, pClESR, was constructed by designing and synthesizing oligonucleotide primers from sequences in the 5' and 3' flanking regions of the ERα gene (see primers below). Primers ESR5'F and ESR5'R were synthesized with recognition sequences for HinduIII and MluI, respectively, at their 5' ends. This set of primers amplifies a 518 bp sequence from the 5' flanking region of the ER gene. Primers ESR3'F and ESR3'R were synthesized with recognition sequences for BamHI and NotI, respectively, at their 5' ends. This set of primers amplifies a 462 bp sequence from the 3' flanking region of the ER gene. The amplified sequences were digested with the appropriate enzymes and cloned into pClasper in a head-to-tail manner. The completed pClESR vector was linearized with BamHI and MluI prior to co-transformation of yeast with uncloned, native genomic DNA.

containing a promoterless lacZ gene and a URA3 gene was inserted in frame in the first exon of Hoxc8, rather than the second exon as previously described (Bradshaw et al., 1996). The insert of pClC9C6-Exon 1 contains 25.5 kb of DNA surrounding the Hoxc8 gene and extending from Hoxc6 to Hoxc9. The insert was excised from the vector by I-SceI digestion, purified by sucrose gradient, and injected into one-cell mouse embryos for the production of transgenic mice. All procedures for producing transgenic mice and analyzing the transgene were as described in Shashikant et al. (1995). A permanent transgenic mouse line was established propagating the Hoxc8 lacZ-URA3 reporter gene.

Figure 16:
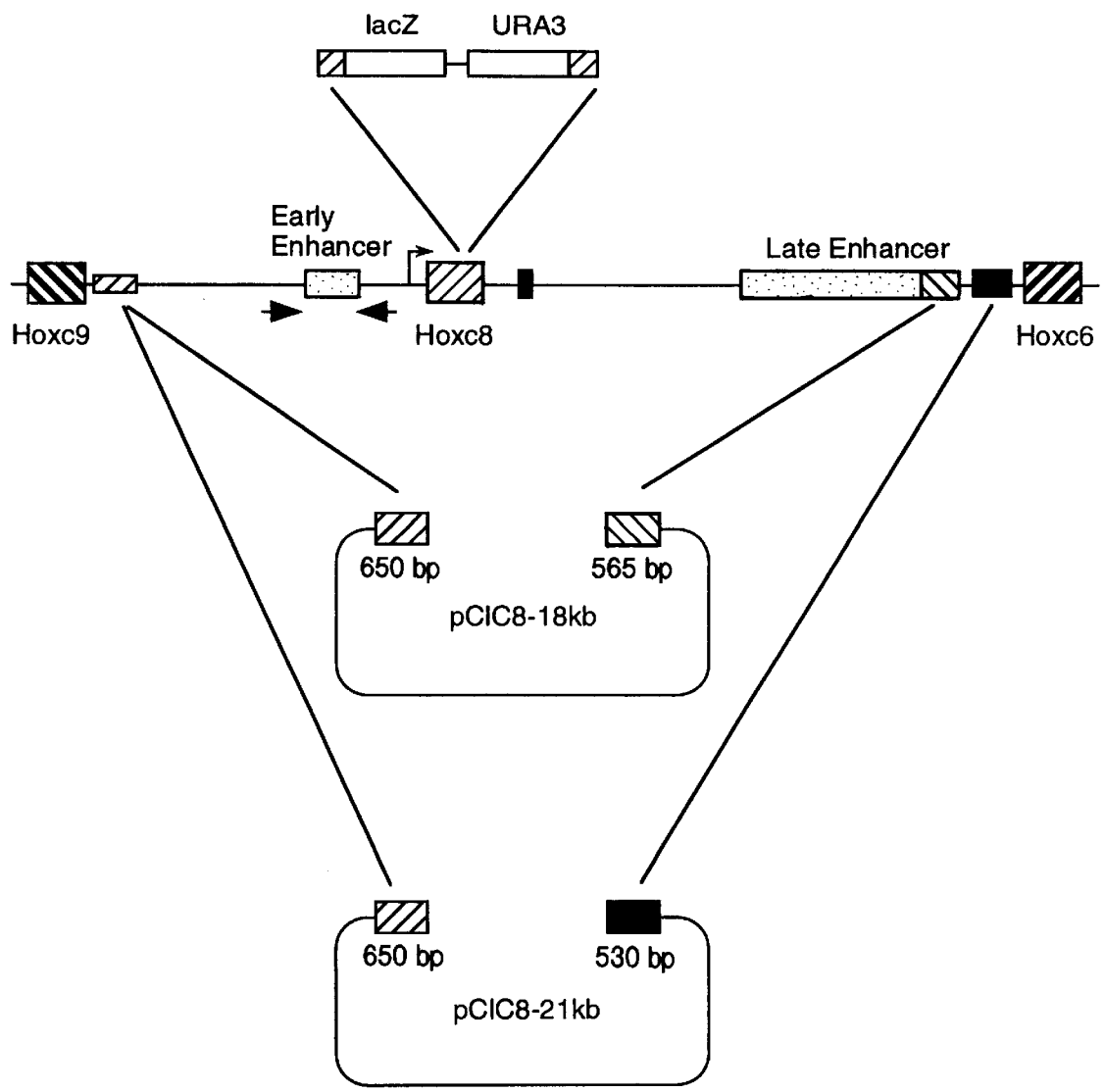
FIG. 16. Construction of Hoxc8 Claspers, pClC8-18 kb and pClC8-21 kb. Two Claspers were constructed to recover regions of 18 and 21 kb from native genomic DNA derived from transgenic mice carrying the lacZ-URA3 reporter in the Hoxc8 gene. The Claspers were constructed with identical 650 bp arms anchored at the Hoxc9 gene. pClC8-18 kb had a 565 bp recombinogenic arm from the 5' flanking region of Hoxc6. pClC8-21 kb had a 530 bp recombinogenic arm from a sequence approximately 3 kb downstream from the 565 bp site. Arrowheads indicate the 400 bp probe from the early enhancer region used to analyze recombinants.

To demonstrate TIVC, two pClasper vectors (FIG. 16) were constructed and used to co-transform yeast spheroplasts in the presence of genomic DNA prepared from Hoxc8 lacZ-URA3 transgenic mice for the purpose of recovering either an 18 kb or 21 kb region containing the Hoxc-8 lacZ-URA3 (note that the lacZ-URA3 reporter adds an additional 5 kb to the size of the recovered fragment, 23 and 26 kb, respectively). The two pClasper vectors were constructed with the identical 650 bp recombinogenic ends amplified form 5' flanking sequence of the Hoxc9 gene (see primers below). The 5' and 3' primers of the 650 bp amplicon were constructed with BamHI and NruI recognition sites, respectively. Clasper, pClC8-18 kb, was constructed with a 565 bp recombinogenic arm amplified from the 3' flanking region of Hoxc6. Clasper, pClC8-21 kb, was constructed

```
ESR5'F nt 156-175    5' CAG AAA GCA GTC AAC TGA GC 3'
ESR5'R nt 655-674    5' AGC GCT GGA TGA ATG GCA G 3'
ESR3'F nt 2958-2976  5' TAG CCA GGA TGG TCT CGA TC 3'
ESR3'R nt 3401-3420  5' AAT TCG TTA CTA GTA GAC CCA C 3'
```

EXAMPLE 7
Haplotyping by TIVC and Creation of a Genome Anthology from Population Tubes.

Pooling DNA from individuals of genetically and geographically divergent human populations and the subsequent recovery of haplotypes by the TIVC approach, is analogous to, and a logical extension of, detecting specific DNA sequences by en masse PCR amplification of "population tubes" mimicking interpopulation mixing (Ruano et al., 1994).

To accomplish the pooling step, DNAs were purified from lymphocyte cell cultures of twelve individuals from CEPH Family 13294. Family 13294 spans three generations. DNAs from individual family members were purified as high molecular weight preparations by phenol-chloroform extraction, and as intact chromosomal DNA by embedding the cells in low-melting temperature agarose followed by proteinase K treatment (Bentley et al., 1990). DNAs were used individually and in pools to generate a genome anthology for the Endothelin-1 gene. Equivalent amounts of DNA from each individual were mixed to form the pool (n=12). Endothelin-1 haplotypes were recovered from the pooled DNA by TIVC, and the resulting frequencies were compared with the haplotypes derived from individual samples.

EXAMPLE 8

Bradshaw et al. (1995) constructed the pClasper vector pClC9C6, to recover a 25.5 kb fragment containing the mouse Hoxc8 gene from a 440 kb yeast artificial chromosome. A Hoxc8-lacZ construct was generated by homologous recombination using the methods described in Bradshaw et al. (1996). In this example, the 5 kb cassette, with a 530 bp recombinogenic arm from the 3' flanking region of Hoxc6, approximately 3 kb downstream from the 565 bp site used for pClC8-18 kb.

Figure 13B:
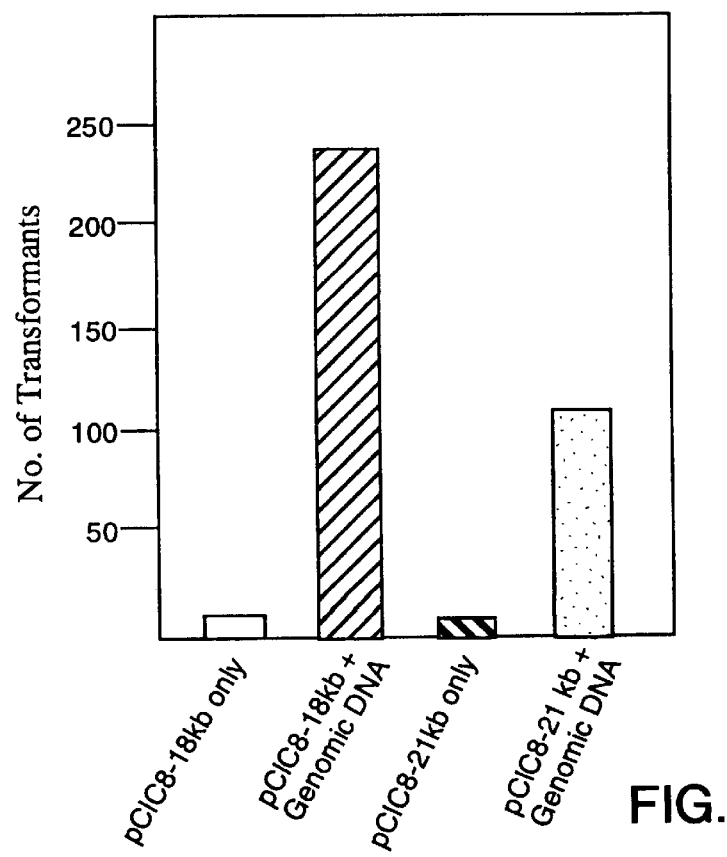
Figure 17A:
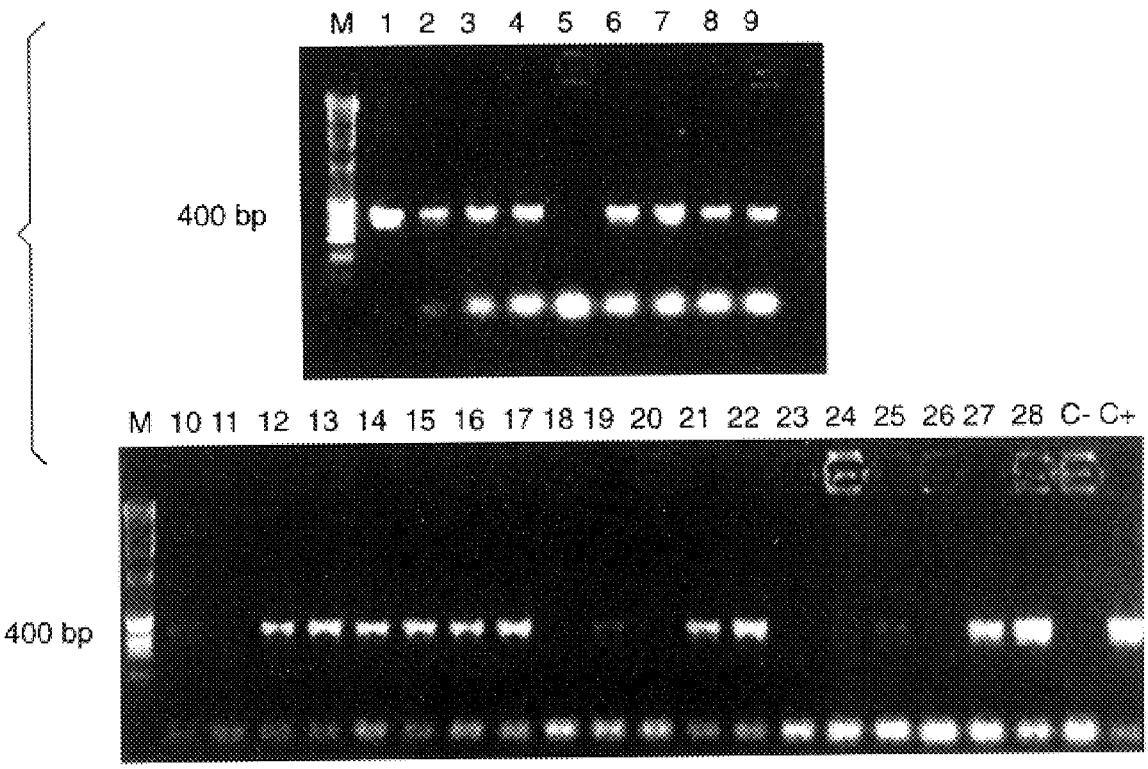
FIG. 17. PCR analysis of Hoxc8 lacZ-URA3 recombinants. Transformants were analyzed by colony PCR using primers that amplified a 400 bp region from the Hoxc8 early enhancer region.
Figure 17B:
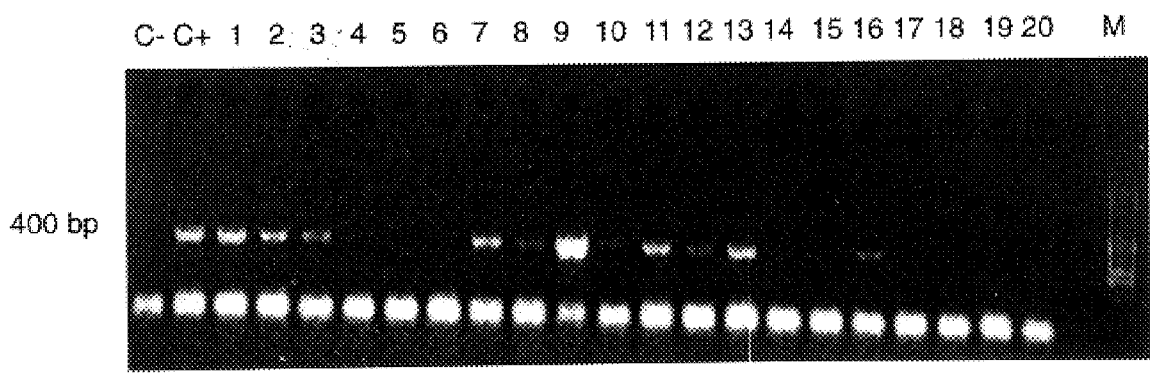

Using the optimized co-transformation protocol described in Example 1, parallel experiments were performed in which yeast spheroplasts were co-transformed with either pClC8-18Kb or pClC8-21 kb and total native genomic DNA from Hoxc8-lacZ transgenic mice, or pClC8-18 kb or pClC8-21 kb and native genomic DNA strain 129svj mice. Vector and genomic DNA were mixed at ratios of 1:5 and 1:10. Transformants from Hoxc8-lacZ mice were selected on leu⁻/ura⁻ medium, a double selection was made possible by the LEU2 gene in the Clasper vector and the URA3 gene inserted in the Hoxc8 gene of the transgenic DNA. Transformants from 129svj mice were selected on leu⁻ medium. The results in FIG. 13B illustrate the numbers of transformants observed on experimental versus control plates (vector only). Ten to twenty fold more transformants were observed on plates carrying potential recombinants. Transformants were analyzed by colony PCR using primers that amplified a 400 bp region from the Hoxc8 early enhancer region (Shashikant and Ruddle, 1996). FIG. 17 shows the results of PCR analysis of recombinants containing the Hoxc8 gene. Well over 50% of the potential recombinants observed on the selection plates were positive for amplification of this region of Hoxc8, indicating that recombination had taken place. These results demonstrate the utility of the TIVC method for targeting and rescuing a specific locus from uncloned native genomic DNA.

650 bp Arm (used for both pClC8-18 kb and PClC8-21 kb)
5' primer 5' ATG GAT CCG ACA AGG AAC AAA TCC TAA GCC C 3' BamHI
3' primer 3' GTC GCG ATG CAT TTG CAG CCT GAT CCA GCC A 3' NruI 565 bP Arm (used for PClC8-18 kb)
5' primer 5' TCG CGA CTC AGA CCT GCC CCT TAA GAG 3' NruI
3' primer 5' AAG CTT GAG CCT CTG AGT TGG CAG ACT TCA TGG 3' Hind
530 bp Arm (used for pClC8-21 kb)
5' primer 5' TCG CGA GGC ATC AAG GTG GAA GGG AGG CTC 3' NruI
3' primer 5' AAG CTT AAA GAT ACT TGA AGA AAC GTG 3' HindIII

References

Adachi, et al., 1993 *J. Cardiovascular Pharm.* 22 (Suppl. 8):S121–S124.
Aquadro, et al., 1991 *Proc. Natl. Acad. Sci. USA* 88:305–309.
Arai, et al., 1993 *J. Biol. Chem.* 268:3463–3470.
Arinami, et al., 1991 *Am. J. Hum. Genet.* 48:990–996.
Barnes, 1994 *Proc. Natl. Acad. Sci. USA* 91:2216–2220.
Bentley, et al., 1990 *Methods in Nucleic Acid Research*, Karam, Chao and Warr, eds., CRC Press, Inc., Boca Raton, Fla., pp. 131–156.
Botstein, et al. 1980 *Am. J. Hum. Genet* 32:314–331.
Bowcock, et al. 1987 *Gene Geography* 1:47–64.
Bradshaw, M. S., et al., 1995 *Nucl. Acids Res.* 23:4850–4856.
Burgers and Percival, 1987 *Analyt. Biochem.* 163:391–397.
Cheng, et al., 1994 *Proc. Natl. Acad. Sci. USA* 91:5695–5699.
Collins, 1995 *Nature Genet.* 9:3477–350.
Dubovsky, et al., 1995 *Hum. Mol. Genet.* 4:449–452.
Excoffier, et al., 1995 *Mol. Biol. Evol.* 12:921–927.
Harrington, et al., 1997 *Nature Genet.* 15:345–355.
Hosoda, et al., 1992 *J. Biol. Chem.* 267:18797–18804.
Huxley, 1997 *Trends Genet.* 13:345–347.
Ioannou, et al., 1994 *Nature Genet.* 6:84–89.
Jankowsky, et al., 1997 *Nucl. Acids Res.* 25:2690–2693.
Kogoma, 1997 *Microbiol Mol. Biol. Reviews* 61:212–238.
Krietman, 1983 *Nature* 304:412–417.
Kuiper, et al., 1996 *Endocrinology* 138:863–870.
Lander, et al. 1989 *Genetics* 121:185–199.
Levin, 1995 *New Eng. J. Med.* 333:356–363.
Mansour, et al., 1988 *Nature* 336:348–352.
McDonnel, et al., 1993 *Bio/Technology* 11:1256–1261.
Mosselman, et al., 1996 *FEBS Letters* 392:49–53.
Orr-Weaver, et al., 1981 *Proc. Natl. Acad. Sci., USA* 78:6354–6358.
Orr-Weaver, et al., 1983 *Meth. Enzymol.* 101:228–245.
Ponglikitmongkol, et al., 1988 *EMBO J.* 7:3385–3388.
Riley, et al., 1989 *Genetics* 123:359–369.
Rosenfield, 1997 *Nature Genet.,* 15:333.
Ruano, 1994, *PCR Methods & Applications* 3:225–231.
Sambrook, et al., 1989 *Molecular Cloning*, 2nd Ed.
Shashikant et al., 1995 *Development* 121:4339–4347
Shashikant and Ruddle 1996 *Proc. Natl. Acad. Sci., USA* 93:12364–12369.
Shinohara, et al., 1993 *Nature Genet.* 4:239–243.
Sternberg, 1990 *Proc. Natl. Acad. Sci., USA* 87:103–107.
Stinchcomb, et al., 1980 *Proc. Natl. Acad. Sci., USA* 77:4559–4563.
Templeton, et al., 1987 *Genetics*, 117:343–350.
Tishkoff, et al., 1996a *Science* 271:1380–1387.
Tishkoff, et al., 1996b *Am. J. Hum. Genet.* 59 (suppl.):A191.
Weber, J. L. and P. E. May, 1989 *Am. J. Hum. Genet.* 44:388–396.

We claim:

1. A method of generating genome anthologies consisting of the steps of:
   a. obtaining a plurality of native genomic DNA samples from different sources;
   b. targeting a DNA locus within said DNA samples; and
   c. isolating said DNA locus from said DNA samples, thereby producing a genome anthology.

2. The method of claim 1 wherein the plurality of DNA samples is obtained by pooling DNA samples from different sources.

3. The method of claim 1 wherein targeting and isolation steps are carried out simultaneously using targeted in vivo cloning.

4. A method for generating a genome anthology using targeted in vivo cloning comprising the steps of:
   a. linearizing a vector, said vector comprising a bacterial replication origin, a bacterial marker gene, a yeast replication origin, a yeast centromere sequence, a yeast marker gene, a unique cloning site and recombinogenic ends homologous to specific regions of a target DNA locus;
   b. introducing said linearized vector and a target sequence into yeast cells, said target sequence consistingz of native genomic DNA, such that homologous recombination occurs in the yeast cells, said homologous recombination resulting in formation of circular hemizygous clones;
   c. shuttling said circular hemizygous clones into bacterial cells; and
   d. amplifying hemizygous clones, thereby producing a genome anthology.

* * * * *

UNITED STATES PATENT AND TRADEMARK OFFICE
CERTIFICATE OF CORRECTION

PATENT NO.   : 5,972,614
DATED        : October 26, 1999
INVENTOR(S)  : Gualberto Ruano, et. al.

It is certified that error appears in the above-identified patent and that said Letters Patent is hereby corrected as shown below:

Title page, item [73], Assignee: --add Yale University--.

Signed and Sealed this

Sixth Day of June, 2000

Attest:

Q. TODD DICKINSON

*Attesting Officer*          *Director of Patents and Trademarks*